(12) United States Patent
Whitfield et al.

(10) Patent No.: US 12,702,411 B2
(45) **Date of Patent: *Aug. 11, 2026**

(54) REPLACEABLE STAPLE CARTRIDGE WITH RETRACTABLE KNIFE

(71) Applicant: Covidien LP, Mansfield, MA (US)

(72) Inventors: Kenneth H. Whitfield, North Haven, CT (US); Roanit A. Fernandes, Hamden, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/952,648

(22) Filed: Nov. 19, 2024

(65) Prior Publication Data

US 2025/0072896 A1 Mar. 6, 2025

Related U.S. Application Data

(63) Continuation of application No. 17/826,271, filed on May 27, 2022, now Pat. No. 12,193,666.

(51) Int. Cl.
*A61B 17/072* (2006.01)

(52) U.S. Cl.
CPC .................. *A61B 17/07207* (2013.01); *A61B 2017/07257* (2013.01); *A61B 2017/07278* (2013.01)

(58) Field of Classification Search
CPC ............ A61B 17/072; A61B 17/07207; A61B 2017/07257; A61B 2017/07278; A61B 2017/07285; A61B 2017/07271
USPC ...................................................... 227/175.1
See application file for complete search history.

(56) References Cited

U.S. PATENT DOCUMENTS

| | | | |
|---|---|---|---|
| 3,499,591 | A | 3/1970 | Green |
| 3,777,538 | A | 12/1973 | Weatherly et al. |
| 3,882,854 | A | 5/1975 | Hulka et al. |
| 4,027,510 | A | 6/1977 | Hiltebrandt |
| 4,086,926 | A | 5/1978 | Green et al. |
| 4,241,861 | A | 12/1980 | Fleischer |
| 4,244,372 | A | 1/1981 | Kapitanov et al. |
| 4,429,695 | A | 2/1984 | Green |
| 4,505,414 | A | 3/1985 | Filipi |
| 4,520,817 | A | 6/1985 | Green |
| 4,589,413 | A | 5/1986 | Malyshev et al. |
| 4,596,351 | A | 6/1986 | Fedotov et al. |
| 4,602,634 | A | 7/1986 | Barkley |
| 4,605,001 | A | 8/1986 | Rothfuss et al. |

(Continued)

FOREIGN PATENT DOCUMENTS

| | | |
|---|---|---|
| AU | 198654765 | 9/1986 |
| CA | 2773414 A1 | 11/2012 |

(Continued)

*Primary Examiner* — Linda J. Hodge

(57) ABSTRACT

A surgical stapling device includes a tool assembly having a drive assembly, an anvil, and a cartridge assembly. The cartridge assembly includes a replaceable staple cartridge that includes an actuation sled assembly having an actuation sled, a knife bar, and a retractor link. The retractor link is secured to the knife bar such that the actuation sled assembly is movable through a cartridge body of the staple cartridge. The retractor link is movable from a non-deformed condition disengaged from the drive assembly to a deformed condition engaged with the drive assembly to facilitate retraction of the actuation sled assembly after the stapling device is fired.

20 Claims, 15 Drawing Sheets

(56) References Cited

U.S. PATENT DOCUMENTS 4,608,981 A 9/1986 Rothfuss et al.
4,610,383 A 9/1986 Rothfuss et al.
4,633,861 A 1/1987 Chow et al.
4,633,874 A 1/1987 Chow et al.
4,671,445 A 6/1987 Barker et al.
4,700,703 A 10/1987 Resnick et al.
4,703,887 A 11/1987 Clanton et al.
4,728,020 A 3/1988 Green et al.
4,752,024 A 6/1988 Green et al.
4,784,137 A 11/1988 Kulik et al.
4,863,088 A 9/1989 Redmond et al.
4,869,415 A 9/1989 Fox
4,892,244 A 1/1990 Fox et al.
4,955,959 A 9/1990 Tompkins et al.
4,978,049 A 12/1990 Green
4,991,764 A 2/1991 Mericle
5,014,899 A 5/1991 Presty et al.
5,031,814 A 7/1991 Tompkins et al.
5,040,715 A 8/1991 Green et al.
5,065,929 A 11/1991 Schulze et al.
5,071,430 A 12/1991 de Salis et al.
5,074,454 A 12/1991 Peters
5,083,695 A 1/1992 Foslien et al.
5,084,057 A 1/1992 Green et al.
5,106,008 A 4/1992 Tompkins et al.
5,111,987 A 5/1992 Moeinzadeh et al.
5,129,570 A 7/1992 Schulze et al.
5,141,144 A 8/1992 Foslien et al.
5,156,315 A 10/1992 Green et al.
5,156,614 A 10/1992 Green et al.
5,163,943 A 11/1992 Mohiuddin et al.
5,170,925 A 12/1992 Madden et al.
5,171,247 A 12/1992 Hughett et al.
5,173,133 A 12/1992 Morin et al.
5,180,092 A 1/1993 Crainich
5,188,274 A 2/1993 Moeinzadeh et al.
5,220,928 A 6/1993 Oddsen et al.
5,221,036 A 6/1993 Takase
5,242,457 A 9/1993 Akopov et al.
5,246,156 A 9/1993 Rothfuss et al.
5,253,793 A 10/1993 Green et al.
5,263,629 A 11/1993 Trumbull et al.
RE34,519 E 1/1994 Fox et al.
5,275,323 A 1/1994 Schulze et al.
5,282,807 A 2/1994 Knopfler
5,289,963 A 3/1994 McGarry et al.
5,307,976 A 5/1994 Olson et al.
5,308,576 A 5/1994 Green et al.
5,312,023 A 5/1994 Green et al.
5,318,221 A 6/1994 Green et al.
5,326,013 A 7/1994 Green et al.
5,328,077 A 7/1994 Lou
5,330,486 A 7/1994 Wilk
5,332,142 A 7/1994 Robinson et al.
5,336,232 A 8/1994 Green et al.
5,344,061 A 9/1994 Crainich
5,352,238 A 10/1994 Green et al.
5,356,064 A 10/1994 Green et al.
5,358,506 A 10/1994 Green et al.
5,364,001 A 11/1994 Bryan
5,364,002 A 11/1994 Green et al.
5,364,003 A 11/1994 Williamson, IV
5,366,133 A 11/1994 Geiste
5,376,095 A 12/1994 Ortiz
5,379,933 A 1/1995 Green et al.
5,381,943 A 1/1995 Allen et al.
5,382,255 A 1/1995 Castro et al.
5,383,880 A 1/1995 Hooven
5,389,098 A 2/1995 Tsuruta et al.
5,395,033 A 3/1995 Byrne et al.
5,395,034 A 3/1995 Allen et al.
5,397,046 A 3/1995 Savage et al.
5,397,324 A 3/1995 Carroll et al.
5,403,312 A 4/1995 Yates et al.
5,405,072 A 4/1995 Zlock et al.
5,407,293 A 4/1995 Crainich
5,413,268 A 5/1995 Green et al.
5,415,334 A 5/1995 Williamson et al.
5,415,335 A 5/1995 Knodell, Jr.
5,417,361 A 5/1995 Williamson, IV
5,423,471 A 6/1995 Mastri et al.
5,425,745 A 6/1995 Green et al.
5,431,322 A 7/1995 Green et al.
5,431,323 A 7/1995 Smith et al.
5,433,721 A 7/1995 Hooven et al.
5,441,193 A 8/1995 Gravener
5,445,304 A 8/1995 Plyley et al.
5,447,265 A 9/1995 Vidal et al.
5,452,837 A 9/1995 Williamson, IV et al.
5,456,401 A 10/1995 Green et al.
5,464,300 A 11/1995 Crainich
5,465,895 A 11/1995 Knodel et al.
5,467,911 A 11/1995 Tsuruta et al.
5,470,007 A 11/1995 Plyley et al.
5,470,010 A 11/1995 Rothfuss et al.
5,472,132 A 12/1995 Savage et al.
5,474,566 A 12/1995 Alesi et al.
5,476,206 A 12/1995 Green et al.
5,478,003 A 12/1995 Green et al.
5,480,089 A 1/1996 Blewett
5,482,197 A 1/1996 Green et al.
5,484,095 A 1/1996 Green et al.
5,484,451 A 1/1996 Akopov et al.
5,485,947 A 1/1996 Olson et al.
5,485,952 A 1/1996 Fontayne
5,486,185 A 1/1996 Freitas et al.
5,487,499 A 1/1996 Sorrentino et al.
5,487,500 A 1/1996 Knodel et al.
5,489,058 A 2/1996 Plyley et al.
5,490,856 A 2/1996 Person et al.
5,497,933 A 3/1996 DeFonzo et al.
5,501,689 A 3/1996 Green et al.
5,505,363 A 4/1996 Green et al.
5,507,426 A 4/1996 Young et al.
5,518,163 A 5/1996 Hooven
5,518,164 A 5/1996 Hooven
5,529,235 A 6/1996 Boiarski et al.
5,531,744 A 7/1996 Nardella et al.
5,535,934 A 7/1996 Boiarski et al.
5,535,935 A 7/1996 Vidal et al.
5,535,937 A 7/1996 Boiarski et al.
5,540,375 A 7/1996 Bolanos et al.
5,542,594 A 8/1996 McKean et al.
5,549,628 A 8/1996 Cooper et al.
5,551,622 A 9/1996 Yoon
5,553,765 A 9/1996 Knodel et al.
5,554,164 A 9/1996 Wilson et al.
5,554,169 A 9/1996 Green et al.
5,560,530 A 10/1996 Bolanos et al.
5,560,532 A 10/1996 DeFonzo et al.
5,562,239 A 10/1996 Boiarski et al.
5,562,241 A 10/1996 Knodel et al.
5,562,682 A 10/1996 Oberlin et al.
5,562,701 A 10/1996 Huitema et al.
5,564,615 A 10/1996 Bishop et al.
5,571,116 A 11/1996 Bolanos et al.
5,573,169 A 11/1996 Green et al.
5,573,543 A 11/1996 Akopov et al.
5,575,799 A 11/1996 Bolanos et al.
5,575,803 A 11/1996 Cooper et al.
5,577,654 A 11/1996 Bishop
5,584,425 A 12/1996 Savage et al.
5,586,711 A 12/1996 Plyley et al.
5,588,580 A 12/1996 Paul et al.
5,588,581 A 12/1996 Conlon et al.
5,597,107 A 1/1997 Knodel et al.
5,601,224 A 2/1997 Bishop et al.
5,607,095 A 3/1997 Smith et al.
5,615,820 A 4/1997 Viola
5,618,291 A 4/1997 Thompson et al.
5,624,452 A 4/1997 Yates
5,626,587 A 5/1997 Bishop et al.
5,628,446 A 5/1997 Geiste et al.
5,630,539 A 5/1997 Plyley et al.

(56) References Cited

U.S. PATENT DOCUMENTS 5,630,540 A 5/1997 Blewett
5,630,541 A 5/1997 Williamson, IV et al.
5,632,432 A 5/1997 Schulze et al.
5,634,584 A 6/1997 Okorocha et al.
5,636,780 A 6/1997 Green et al.
5,645,209 A 7/1997 Green et al.
5,647,526 A 7/1997 Green et al.
5,651,491 A 7/1997 Heaton et al.
5,653,373 A 8/1997 Green et al.
5,653,374 A 8/1997 Young et al.
5,653,721 A 8/1997 Knodel et al.
5,655,698 A 8/1997 Yoon
5,657,921 A 8/1997 Young et al.
5,658,300 A 8/1997 Bito et al.
5,662,258 A 9/1997 Knodel et al.
5,662,259 A 9/1997 Yoon
5,662,260 A 9/1997 Yoon
5,662,662 A 9/1997 Bishop et al.
5,662,666 A 9/1997 Onuki et al.
5,665,085 A 9/1997 Nardella
5,667,517 A 9/1997 Hooven
5,669,544 A 9/1997 Schulze et al.
5,673,840 A 10/1997 Schulze et al.
5,673,841 A 10/1997 Schulze et al.
5,673,842 A 10/1997 Bittner et al.
5,676,674 A 10/1997 Bolanos et al.
5,680,981 A 10/1997 Mililli et al.
5,680,982 A 10/1997 Schulze et al.
5,680,983 A 10/1997 Plyley et al.
5,690,269 A 11/1997 Bolanos et al.
5,690,675 A 11/1997 Sawyer et al.
5,692,668 A 12/1997 Schulze et al.
5,697,542 A 12/1997 Knodel et al.
5,702,409 A 12/1997 Rayburn et al.
5,704,534 A 1/1998 Huitema et al.
5,706,997 A 1/1998 Green et al.
5,709,334 A 1/1998 Sorrentino et al.
5,711,472 A 1/1998 Bryan
5,713,505 A 2/1998 Huitema
5,715,988 A 2/1998 Palmer
5,716,366 A 2/1998 Yates
5,718,359 A 2/1998 Palmer et al.
5,725,536 A 3/1998 Oberlin et al.
5,725,554 A 3/1998 Simon et al.
5,728,110 A 3/1998 Vidal et al.
5,732,806 A 3/1998 Foshee et al.
5,735,848 A 4/1998 Yates et al.
5,743,456 A 4/1998 Jones et al.
5,749,893 A 5/1998 Vidal et al.
5,752,644 A 5/1998 Bolanos et al.
5,762,255 A 6/1998 Chrisman et al.
5,762,256 A 6/1998 Mastri et al.
5,769,303 A 6/1998 Knodel et al.
5,769,892 A 6/1998 Kingwell
5,772,099 A 6/1998 Gravener
5,772,673 A 6/1998 Cuny et al.
5,779,130 A 7/1998 Alesi et al.
5,779,131 A 7/1998 Knodel et al.
5,779,132 A 7/1998 Knodel et al.
5,782,396 A 7/1998 Mastri et al.
5,782,397 A 7/1998 Koukline
5,782,834 A 7/1998 Lucey et al.
5,785,232 A 7/1998 Vidal et al.
5,797,536 A 8/1998 Smith et al.
5,797,537 A 8/1998 Oberlin et al.
5,797,538 A 8/1998 Heaton et al.
5,810,811 A 9/1998 Yates et al.
5,810,855 A 9/1998 Rayburn et al.
5,814,055 A 9/1998 Knodel et al.
5,814,057 A 9/1998 Oi et al.
5,816,471 A 10/1998 Plyley et al.
5,817,109 A 10/1998 McGarry et al.
5,820,009 A 10/1998 Melling et al.
5,823,066 A 10/1998 Huitema et al.
5,826,776 A 10/1998 Schulze et al.
5,829,662 A 11/1998 Allen et al.
5,833,695 A 11/1998 Yoon
5,836,147 A 11/1998 Schnipke
5,862,972 A 1/1999 Green et al.
5,865,361 A 2/1999 Milliman et al.
5,871,135 A 2/1999 Williamson IV et al.
5,873,873 A 2/1999 Smith et al.
5,878,938 A 3/1999 Bittner et al.
5,893,506 A 4/1999 Powell
5,894,979 A 4/1999 Powell
5,897,562 A 4/1999 Bolanos et al.
5,901,895 A 5/1999 Heaton et al.
5,911,352 A 6/1999 Racenet et al.
5,911,353 A 6/1999 Bolanos et al.
5,918,791 A 7/1999 Sorrentino et al.
5,919,198 A 7/1999 Graves, Jr. et al.
5,922,001 A 7/1999 Yoon
5,931,847 A 8/1999 Bittner et al.
5,941,442 A 8/1999 Geiste et al.
5,954,259 A 9/1999 Viola et al.
5,964,774 A 10/1999 McKean et al.
5,980,510 A 11/1999 Tsonton et al.
5,988,479 A 11/1999 Palmer
6,004,335 A 12/1999 Vaitekunas et al.
6,010,054 A 1/2000 Johnson et al.
6,032,849 A 3/2000 Mastri et al.
6,045,560 A 4/2000 McKean et al.
6,063,097 A 5/2000 Oi et al.
6,079,606 A 6/2000 Milliman et al.
6,099,551 A 8/2000 Gabbay
6,109,500 A 8/2000 Alli et al.
6,131,789 A 10/2000 Schulze et al.
6,131,790 A 10/2000 Piraka
6,155,473 A 12/2000 Tompkins et al.
6,197,017 B1 3/2001 Brock et al.
6,202,914 B1 3/2001 Geiste et al.
6,241,139 B1 6/2001 Milliman et al.
6,250,532 B1 6/2001 Green et al.
6,264,086 B1 7/2001 McGuckin, Jr.
6,264,087 B1 7/2001 Whitman
6,279,809 B1 8/2001 Nicolo
6,315,183 B1 11/2001 Piraka
6,315,184 B1 11/2001 Whitman
6,325,810 B1 12/2001 Hamilton et al.
6,330,965 B1 12/2001 Milliman et al.
6,391,038 B2 5/2002 Vargas et al.
6,398,797 B2 6/2002 Bombard et al.
6,436,097 B1 8/2002 Nardella
6,439,446 B1 8/2002 Perry et al.
6,443,973 B1 9/2002 Whitman
6,478,804 B2 11/2002 Vargas et al.
6,488,196 B1 12/2002 Fenton, Jr.
6,503,257 B2 1/2003 Grant et al.
6,505,768 B2 1/2003 Whitman
6,544,274 B2 4/2003 Danitz et al.
6,554,844 B2 4/2003 Lee et al.
6,565,554 B1 5/2003 Niemeyer
6,587,750 B2 7/2003 Gerbi et al.
6,592,597 B2 7/2003 Grant et al.
6,594,552 B1 7/2003 Nowlin et al.
6,602,252 B2 8/2003 Mollenauer
6,619,529 B2 9/2003 Green et al.
D480,808 S 10/2003 Wells et al.
6,644,532 B2 11/2003 Green et al.
6,656,193 B2 12/2003 Grant et al.
6,669,073 B2 12/2003 Milliman et al.
6,681,978 B2 1/2004 Geiste et al.
6,698,643 B2 3/2004 Whitman
6,716,232 B1 4/2004 Vidal et al.
6,722,552 B2 4/2004 Fenton, Jr.
6,755,338 B2 6/2004 Hahnen et al.
6,783,524 B2 8/2004 Anderson et al.
6,786,382 B1 9/2004 Hoffman
6,817,509 B2 11/2004 Geiste et al.
6,830,174 B2 12/2004 Hillstead et al.
6,835,199 B2 12/2004 McGuckin, Jr. et al.
6,843,403 B2 1/2005 Whitman
RE38,708 E 3/2005 Bolanos et al.
6,877,647 B2 4/2005 Green et al.

(56) References Cited

U.S. PATENT DOCUMENTS 6,889,116 B2 5/2005 Jinno
6,905,057 B2 6/2005 Swayze et al.
6,945,444 B2 9/2005 Gresham et al.
6,953,138 B1 10/2005 Dworak et al.
6,953,139 B2 10/2005 Milliman et al.
6,959,852 B2 11/2005 Shelton, IV et al.
6,962,594 B1 11/2005 Thevenet
6,964,363 B2 11/2005 Wales et al.
6,978,921 B2 12/2005 Shelton, IV et al.
6,981,628 B2 1/2006 Wales
6,986,451 B1 1/2006 Mastri et al.
6,988,649 B2 1/2006 Shelton, IV et al.
6,991,627 B2 1/2006 Madhani et al.
6,994,714 B2 2/2006 Vargas et al.
7,000,818 B2 2/2006 Shelton, IV et al.
7,000,819 B2 2/2006 Swayze et al.
7,032,799 B2 4/2006 Viola et al.
7,044,352 B2 5/2006 Shelton, IV et al.
7,044,353 B2 5/2006 Mastri et al.
7,055,730 B2 6/2006 Ehrenfels et al.
7,055,731 B2 6/2006 Shelton, IV et al.
7,059,508 B2 6/2006 Shelton, IV et al.
7,070,083 B2 7/2006 Jankowski
7,083,075 B2 8/2006 Swayze et al.
7,097,089 B2 8/2006 Marczyk
7,111,769 B2 9/2006 Wales et al.
7,114,642 B2 10/2006 Whitman
7,121,446 B2 10/2006 Arad et al.
7,128,253 B2 10/2006 Mastri et al.
7,128,254 B2 10/2006 Shelton, IV et al.
7,140,527 B2 11/2006 Ehrenfels et al.
7,140,528 B2 11/2006 Shelton, IV
7,143,923 B2 12/2006 Shelton, IV et al.
7,143,924 B2 12/2006 Scirica et al.
7,143,925 B2 12/2006 Shelton, IV et al.
7,143,926 B2 12/2006 Shelton, IV et al.
7,147,138 B2 12/2006 Shelton, IV
7,159,750 B2 1/2007 Racenet et al.
7,168,604 B2 1/2007 Milliman et al.
7,172,104 B2 2/2007 Scirica et al.
7,188,758 B2 3/2007 Viola et al.
7,207,471 B2 4/2007 Heinrich et al.
7,213,736 B2 5/2007 Wales et al.
7,225,963 B2 6/2007 Scirica
7,225,964 B2 6/2007 Mastri et al.
7,238,195 B2 7/2007 Viola
7,246,734 B2 7/2007 Shelton, IV
7,258,262 B2 8/2007 Mastri et al.
7,267,682 B1 9/2007 Bender et al.
7,278,562 B2 10/2007 Mastri et al.
7,278,563 B1 10/2007 Green
7,287,682 B1 10/2007 Ezzat et al.
7,293,685 B2 11/2007 Ehrenfels et al.
7,296,722 B2 11/2007 Ivanko
7,296,724 B2 11/2007 Green et al.
7,296,772 B2 11/2007 Wang
7,300,444 B1 11/2007 Nielsen et al.
7,303,107 B2 12/2007 Milliman et al.
7,303,108 B2 12/2007 Shelton, IV
7,308,998 B2 12/2007 Mastri et al.
7,326,232 B2 2/2008 Viola et al.
7,328,828 B2 2/2008 Ortiz et al.
7,328,829 B2 2/2008 Arad et al.
7,334,717 B2 2/2008 Rethy et al.
7,354,447 B2 4/2008 Shelton, IV et al.
7,357,287 B2 4/2008 Shelton, IV et al.
7,364,061 B2 4/2008 Swayze et al.
7,367,485 B2 5/2008 Shelton, IV et al.
7,377,928 B2 5/2008 Zubik et al.
7,380,695 B2 6/2008 Doll et al.
7,380,696 B2 6/2008 Shelton, IV et al.
7,396,356 B2 7/2008 Mollenauer
7,398,907 B2 7/2008 Racenet et al.
7,399,310 B2 7/2008 Edoga et al.
7,401,720 B1 7/2008 Durrani
7,401,721 B2 7/2008 Holsten et al.
7,404,508 B2 7/2008 Smith et al.
7,404,509 B2 7/2008 Ortiz et al.
7,407,074 B2 8/2008 Ortiz et al.
7,407,075 B2 8/2008 Holsten et al.
7,407,077 B2 8/2008 Ortiz et al.
7,407,078 B2 8/2008 Shelton, IV et al.
7,416,101 B2 8/2008 Shelton, IV et al.
7,419,080 B2 9/2008 Smith et al.
7,419,081 B2 9/2008 Ehrenfels et al.
7,419,495 B2 9/2008 Menn et al.
7,422,139 B2 9/2008 Shelton, IV et al.
7,424,965 B2 9/2008 Racenet et al.
7,431,189 B2 10/2008 Shelton, IV et al.
7,431,730 B2 10/2008 Viola
7,434,715 B2 10/2008 Shelton, IV et al.
7,434,717 B2 10/2008 Shelton, IV et al.
7,438,208 B2 10/2008 Larson
7,438,209 B1 10/2008 Hess et al.
7,441,684 B2 10/2008 Shelton, IV et al.
7,441,685 B1 10/2008 Boudreaux
7,448,525 B2 11/2008 Shelton, IV et al.
7,451,904 B2 11/2008 Shelton, IV
7,455,208 B2 11/2008 Wales et al.
7,455,676 B2 11/2008 Holsten et al.
7,458,494 B2 12/2008 Matsutani et al.
7,461,767 B2 12/2008 Viola et al.
7,462,185 B1 12/2008 Knodel
7,464,846 B2 12/2008 Shelton, IV et al.
7,464,847 B2 12/2008 Viola et al.
7,464,848 B2 12/2008 Green et al.
7,464,849 B2 12/2008 Shelton, IV et al.
7,467,740 B2 12/2008 Shelton, IV et al.
7,472,814 B2 1/2009 Mastri et al.
7,472,815 B2 1/2009 Shelton, IV et al.
7,472,816 B2 1/2009 Holsten et al.
7,473,258 B2 1/2009 Clauson et al.
7,481,347 B2 1/2009 Roy
7,481,348 B2 1/2009 Marczyk
7,481,349 B2 1/2009 Holsten et al.
7,481,824 B2 1/2009 Boudreaux et al.
7,487,899 B2 2/2009 Shelton, IV et al.
7,490,749 B2 2/2009 Schall et al.
7,494,039 B2 2/2009 Racenet et al.
7,500,979 B2 3/2009 Hueil et al.
7,503,474 B2 3/2009 Hillstead et al.
7,506,790 B2 3/2009 Shelton, IV
7,506,791 B2 3/2009 Omaits et al.
7,510,107 B2 3/2009 Timm et al.
7,513,408 B2 4/2009 Shelton, IV et al.
7,517,356 B2 4/2009 Heinrich
7,537,602 B2 5/2009 Whitman
7,543,729 B2 6/2009 Ivanko
7,543,730 B1 6/2009 Marczyk
7,543,731 B2 6/2009 Green et al.
7,552,854 B2 6/2009 Wixey et al.
7,556,185 B2 7/2009 Viola
7,556,186 B2 7/2009 Milliman
7,559,450 B2 7/2009 Wales et al.
7,559,452 B2 7/2009 Wales et al.
7,559,453 B2 7/2009 Heinrich et al.
7,559,937 B2 7/2009 de la Torre et al.
7,565,993 B2 7/2009 Milliman et al.
7,568,603 B2 8/2009 Shelton, IV et al.
7,568,604 B2 8/2009 Ehrenfels et al.
7,571,845 B2 8/2009 Viola
7,575,144 B2 8/2009 Ortiz et al.
7,584,880 B2 9/2009 Racenet et al.
7,588,174 B2 9/2009 Holsten et al.
7,588,175 B2 9/2009 Timm et al.
7,588,176 B2 9/2009 Timm et al.
7,588,177 B2 9/2009 Racenet
7,597,229 B2 10/2009 Boudreaux et al.
7,597,230 B2 10/2009 Racenet et al.
7,600,663 B2 10/2009 Green
7,604,150 B2 10/2009 Boudreaux
7,604,151 B2 10/2009 Hess et al.
7,607,557 B2 10/2009 Shelton, IV et al.
7,611,038 B2 11/2009 Racenet et al.

(56) References Cited

U.S. PATENT DOCUMENTS 7,617,961 B2 11/2009 Viola
7,624,902 B2 12/2009 Marczyk et al.
7,624,903 B2 12/2009 Green et al.
7,631,793 B2 12/2009 Rethy et al.
7,631,794 B2 12/2009 Rethy et al.
7,635,073 B2 12/2009 Heinrich
7,635,074 B2 12/2009 Olson et al.
7,635,373 B2 12/2009 Ortiz
7,637,409 B2 12/2009 Marczyk
7,637,410 B2 12/2009 Marczyk
7,641,091 B2 1/2010 Olson et al.
7,641,095 B2 1/2010 Viola
7,644,848 B2 1/2010 Swayze et al.
7,648,055 B2 1/2010 Marczyk
7,651,017 B2 1/2010 Ortiz et al.
7,654,431 B2 2/2010 Hueil et al.
7,658,311 B2 2/2010 Boudreaux
7,658,312 B2 2/2010 Vidal et al.
7,665,646 B2 2/2010 Prommersberger
7,665,647 B2 2/2010 Shelton, IV et al.
7,669,746 B2 3/2010 Shelton, IV
7,670,334 B2 3/2010 Hueil et al.
7,673,780 B2 3/2010 Shelton, IV et al.
7,673,781 B2 3/2010 Swayze et al.
7,673,782 B2 3/2010 Hess et al.
7,673,783 B2 3/2010 Morgan et al.
7,678,121 B1 3/2010 Knodel
7,681,772 B2 3/2010 Green et al.
7,682,367 B2 3/2010 Shah et al.
7,682,368 B1 3/2010 Bombard et al.
7,690,547 B2 4/2010 Racenet et al.
7,694,865 B2 4/2010 Scirica
7,699,205 B2 4/2010 Ivanko
7,703,653 B2 4/2010 Shah et al.
7,721,931 B2 5/2010 Shelton, IV et al.
7,721,933 B2 5/2010 Ehrenfels et al.
7,721,935 B2 5/2010 Racenet et al.
7,726,537 B2 6/2010 Olson et al.
7,726,538 B2 6/2010 Holsten et al.
7,726,539 B2 6/2010 Holsten et al.
7,731,072 B2 6/2010 Timm et al.
7,735,703 B2 6/2010 Morgan et al.
7,740,159 B2 6/2010 Shelton, IV et al.
7,740,160 B2 6/2010 Viola
7,743,960 B2 6/2010 Whitman et al.
7,744,628 B2 6/2010 Viola
7,753,245 B2 7/2010 Boudreaux et al.
7,753,248 B2 7/2010 Viola
7,757,924 B2 7/2010 Gerbi et al.
7,757,925 B2 7/2010 Viola et al.
7,762,445 B2 7/2010 Heinrich et al.
7,766,209 B2 8/2010 Baxter, III et al.
7,766,210 B2 8/2010 Shelton, IV et al.
7,766,924 B1 8/2010 Bombard et al.
7,766,928 B2 8/2010 Ezzat et al.
7,770,774 B2 8/2010 Mastri et al.
7,770,775 B2 8/2010 Shelton, IV et al.
7,776,060 B2 8/2010 Mooradian et al.
7,780,055 B2 8/2010 Scirica et al.
7,784,662 B2 8/2010 Wales et al.
7,789,283 B2 9/2010 Shah
7,789,889 B2 9/2010 Zubik et al.
7,793,812 B2 9/2010 Moore et al.
7,793,814 B2 9/2010 Racenet et al.
7,794,475 B2 9/2010 Hess et al.
7,798,385 B2 9/2010 Boyden et al.
7,798,386 B2 9/2010 Schall et al.
7,799,039 B2 9/2010 Shelton, IV et al.
7,810,690 B2 10/2010 Bilotti et al.
7,810,692 B2 10/2010 Hall et al.
7,810,693 B2 10/2010 Broehl et al.
7,815,090 B2 10/2010 Marczyk
7,815,091 B2 10/2010 Marczyk
7,815,092 B2 10/2010 Whitman et al.
7,819,296 B2 10/2010 Hueil et al.
7,819,297 B2 10/2010 Doll et al.
7,819,298 B2 10/2010 Hall et al.
7,819,299 B2 10/2010 Shelton, IV et al.
7,819,896 B2 10/2010 Racenet
7,823,760 B2 11/2010 Zemlok et al.
7,823,761 B2 11/2010 Boyden et al.
7,824,426 B2 11/2010 Racenet et al.
7,828,186 B2 11/2010 Wales
7,828,187 B2 11/2010 Green et al.
7,828,188 B2 11/2010 Jankowski
7,828,189 B2 11/2010 Holsten et al.
7,832,408 B2 11/2010 Shelton, IV et al.
7,832,611 B2 11/2010 Boyden et al.
7,832,612 B2 11/2010 Baxter, III et al.
7,834,630 B2 11/2010 Damadian et al.
7,837,079 B2 11/2010 Holsten et al.
7,837,081 B2 11/2010 Holsten et al.
7,841,503 B2 11/2010 Sonnenschein et al.
7,845,533 B2 12/2010 Marczyk et al.
7,845,534 B2 12/2010 Viola et al.
7,845,535 B2 12/2010 Scircia
7,845,537 B2 12/2010 Shelton, IV et al.
7,845,538 B2 12/2010 Whitman
7,850,703 B2 12/2010 Bombard et al.
7,857,183 B2 12/2010 Shelton, IV
7,857,184 B2 12/2010 Viola
7,857,185 B2 12/2010 Swayze et al.
7,857,186 B2 12/2010 Baxter, III et al.
7,861,906 B2 1/2011 Doll et al.
7,861,907 B2 1/2011 Green et al.
7,866,524 B2 1/2011 Krehel
7,866,525 B2 1/2011 Scirica
7,866,526 B2 1/2011 Green et al.
7,866,527 B2 1/2011 Hall et al.
7,866,528 B2 1/2011 Olson et al.
7,870,989 B2 1/2011 Viola et al.
7,886,952 B2 2/2011 Scirica et al.
7,891,532 B2 2/2011 Mastri et al.
7,891,533 B2 2/2011 Green et al.
7,891,534 B2 2/2011 Wenchell et al.
7,896,214 B2 3/2011 Farascioni
7,900,805 B2 3/2011 Shelton, IV et al.
7,901,416 B2 3/2011 Nolan et al.
7,905,380 B2 3/2011 Shelton, IV et al.
7,905,381 B2 3/2011 Baxter, III et al.
7,909,039 B2 3/2011 Hur
7,909,220 B2 3/2011 Viola
7,909,221 B2 3/2011 Viola et al.
7,909,224 B2 3/2011 Prommersberger
7,913,891 B2 3/2011 Doll et al.
7,913,893 B2 3/2011 Mastri et al.
7,914,543 B2 3/2011 Roth et al.
7,918,230 B2 4/2011 Whitman et al.
7,922,061 B2 4/2011 Shelton, IV et al.
7,922,063 B2 4/2011 Zemlok et al.
7,922,064 B2 4/2011 Boyden et al.
7,926,691 B2 4/2011 Viola et al.
7,926,692 B2 4/2011 Racenet et al.
7,934,628 B2 5/2011 Wenchell et al.
7,934,630 B2 5/2011 Shelton, IV et al.
7,934,631 B2 5/2011 Balbierz et al.
7,942,300 B2 5/2011 Rethy et al.
7,942,303 B2 5/2011 Shah
7,950,560 B2 5/2011 Zemlok et al.
7,950,561 B2 5/2011 Aranyi
7,950,562 B2 5/2011 Beardsley et al.
7,954,682 B2 6/2011 Giordano et al.
7,954,683 B1 6/2011 Knodel et al.
7,954,684 B2 6/2011 Boudreaux
7,954,685 B2 6/2011 Viola
7,954,686 B2 6/2011 Baxter, III et al.
7,954,687 B2 6/2011 Zemlok et al.
7,959,051 B2 6/2011 Smith et al.
7,963,431 B2 6/2011 Scirica
7,963,432 B2 6/2011 Knodel et al.
7,963,433 B2 6/2011 Whitman et al.
7,967,178 B2 6/2011 Scirica et al.
7,967,179 B2 6/2011 Olson et al.
7,967,180 B2 6/2011 Scirica

(56) References Cited

U.S. PATENT DOCUMENTS 7,975,894 B2 7/2011 Boyden et al.
7,980,443 B2 7/2011 Scheib et al.
7,988,026 B2 8/2011 Knodel et al.
7,988,027 B2 8/2011 Olson et al.
7,988,028 B2 8/2011 Farascioni et al.
7,992,758 B2 8/2011 Whitman et al.
7,997,468 B2 8/2011 Farascioni
7,997,469 B2 8/2011 Olson et al.
8,002,795 B2 8/2011 Beetel
8,006,885 B2 8/2011 Marczyk
8,006,887 B2 8/2011 Marczyk
8,007,505 B2 8/2011 Weller et al.
8,007,513 B2 8/2011 Nalagatla et al.
8,011,550 B2 9/2011 Aranyi et al.
8,011,551 B2 9/2011 Marczyk et al.
8,011,552 B2 9/2011 Ivanko
8,011,553 B2 9/2011 Mastri et al.
8,011,555 B2 9/2011 Tarinelli et al.
8,012,170 B2 9/2011 Whitman et al.
8,015,976 B2 9/2011 Shah
8,016,177 B2 9/2011 Bettuchi et al.
8,016,178 B2 9/2011 Olson et al.
8,020,742 B2 9/2011 Marczyk
8,020,743 B2 9/2011 Shelton, IV
8,028,882 B2 10/2011 Viola
8,028,883 B2 10/2011 Stopek
8,028,884 B2 10/2011 Sniffin et al.
8,033,438 B2 10/2011 Scirica
8,033,440 B2 10/2011 Wenchell et al.
8,033,441 B2 10/2011 Marczyk
8,033,442 B2 10/2011 Racenet et al.
8,034,077 B2 10/2011 Smith et al.
8,038,044 B2 10/2011 Viola
8,038,045 B2 10/2011 Bettuchi et al.
8,052,024 B2 11/2011 Viola et al.
8,056,787 B2 11/2011 Boudreaux et al.
8,056,788 B2 11/2011 Mastri et al.
8,056,791 B2 11/2011 Whitman
8,061,577 B2 11/2011 Racenet et al.
8,066,166 B2 11/2011 Demmy et al.
8,070,033 B2 12/2011 Milliman et al.
8,070,034 B1 12/2011 Knodel
8,070,035 B2 12/2011 Holsten et al.
8,074,858 B2 12/2011 Marczyk
8,074,859 B2 12/2011 Kostrzewski
8,074,862 B2 12/2011 Shah
8,083,118 B2 12/2011 Milliman et al.
8,083,119 B2 12/2011 Prommersberger
8,083,120 B2 12/2011 Shelton, IV et al.
8,087,563 B2 1/2012 Milliman et al.
8,091,753 B2 1/2012 Viola
8,091,754 B2 1/2012 Ehrenfels et al.
8,091,756 B2 1/2012 Viola
8,092,493 B2 1/2012 Marczyk
8,096,459 B2 1/2012 Ortiz et al.
8,096,460 B2 1/2012 Blier et al.
8,100,309 B2 1/2012 Marczyk
8,100,310 B2 1/2012 Zemlok
8,102,008 B2 1/2012 Wells
8,113,405 B2 2/2012 Milliman
8,113,406 B2 2/2012 Holsten et al.
8,113,407 B2 2/2012 Holsten et al.
8,113,408 B2 2/2012 Wenchell et al.
8,113,409 B2 2/2012 Cohen et al.
8,113,410 B2 2/2012 Hall et al.
8,123,101 B2 2/2012 Racenet et al.
8,127,975 B2 3/2012 Olson et al.
8,127,976 B2 3/2012 Scirica et al.
8,132,703 B2 3/2012 Milliman et al.
8,132,705 B2 3/2012 Viola et al.
8,132,706 B2 3/2012 Marczyk et al.
8,136,713 B2 3/2012 Hathaway et al.
8,141,762 B2 3/2012 Bedi et al.
8,152,041 B2 4/2012 Kostrzewski
8,157,148 B2 4/2012 Scirica
8,157,150 B2 4/2012 Viola et al.
8,157,151 B2 4/2012 Ingmanson et al.
8,157,152 B2 4/2012 Holsten et al.
8,162,197 B2 4/2012 Mastri et al.
8,167,185 B2 5/2012 Shelton, IV et al.
8,167,186 B2 5/2012 Racenet et al.
8,172,121 B2 5/2012 Krehel
8,172,124 B2 5/2012 Shelton, IV et al.
8,181,837 B2 5/2012 Roy
8,186,555 B2 5/2012 Shelton, IV et al.
8,186,557 B2 5/2012 Cohen et al.
8,186,558 B2 5/2012 Sapienza
8,186,559 B1 5/2012 Whitman
8,186,560 B2 5/2012 Hess et al.
8,193,044 B2 6/2012 Kenneth
8,196,795 B2 6/2012 Moore et al.
8,196,796 B2 6/2012 Shelton, IV et al.
8,201,721 B2 6/2012 Zemlok et al.
8,205,619 B2 6/2012 Shah et al.
8,205,780 B2 6/2012 Sorrentino et al.
8,205,781 B2 6/2012 Baxter, III et al.
8,210,412 B2 7/2012 Marczyk
8,210,416 B2 7/2012 Milliman et al.
8,215,532 B2 7/2012 Marczyk
8,216,236 B2 7/2012 Heinrich et al.
8,220,688 B2 7/2012 Laurent et al.
8,220,690 B2 7/2012 Hess et al.
8,225,979 B2 7/2012 Farascioni et al.
8,231,040 B2 7/2012 Zemlok et al.
8,231,041 B2 7/2012 Marczyk et al.
8,235,272 B2 8/2012 Nicholas et al.
8,235,273 B2 8/2012 Olson et al.
8,235,274 B2 8/2012 Cappola
8,236,010 B2 8/2012 Ortiz et al.
8,240,536 B2 8/2012 Marczyk
8,240,537 B2 8/2012 Marczyk
8,241,322 B2 8/2012 Whitman et al.
8,245,897 B2 8/2012 Tzakis et al.
8,245,898 B2 8/2012 Smith et al.
8,245,899 B2 8/2012 Swensgard et al.
8,245,931 B2 8/2012 Shigeta
8,252,009 B2 8/2012 Weller et al.
8,256,653 B2 9/2012 Farascioni
8,256,654 B2 9/2012 Bettuchi et al.
8,256,655 B2 9/2012 Sniffin et al.
8,256,656 B2 9/2012 Milliman et al.
8,267,300 B2 9/2012 Boudreaux
8,272,551 B2 9/2012 Knodel et al.
8,272,553 B2 9/2012 Mastri et al.
8,272,554 B2 9/2012 Whitman et al.
8,276,594 B2 10/2012 Shah
8,276,801 B2 10/2012 Zemlok et al.
8,281,973 B2 10/2012 Wenchell et al.
8,286,847 B2 10/2012 Taylor
8,286,848 B2 10/2012 Wenchell et al.
8,286,850 B2 10/2012 Viola
8,292,146 B2 10/2012 Holsten et al.
8,292,147 B2 10/2012 Viola
8,292,148 B2 10/2012 Viola
8,292,149 B2 10/2012 Ivanko
8,292,150 B2 10/2012 Bryant
8,292,151 B2 10/2012 Viola
8,292,152 B2 10/2012 Milliman et al.
8,292,153 B2 10/2012 Jankowski
8,292,154 B2 10/2012 Marczyk
8,292,155 B2 10/2012 Shelton, IV et al.
8,292,156 B2 10/2012 Kostrzewski
8,292,158 B2 10/2012 Sapienza
8,308,040 B2 11/2012 Huang et al.
8,308,041 B2 11/2012 Kostrzewski
8,308,042 B2 11/2012 Aranyi
8,308,043 B2 11/2012 Bindra et al.
8,308,044 B2 11/2012 Viola
8,308,046 B2 11/2012 Prommersberger
8,308,757 B2 11/2012 Hillstead et al.
8,317,070 B2 11/2012 Hueil et al.
8,317,071 B1 11/2012 Knodel
8,322,455 B2 12/2012 Shelton, IV et al.
8,322,589 B2 12/2012 Boudreaux

(56) References Cited

U.S. PATENT DOCUMENTS 8,328,061 B2 12/2012 Kasvikis
8,328,065 B2 12/2012 Shah
8,333,313 B2 12/2012 Boudreaux et al.
8,336,751 B2 12/2012 Scirica
8,336,753 B2 12/2012 Olson et al.
8,336,754 B2 12/2012 Cappola et al.
8,342,377 B2 1/2013 Milliman et al.
8,342,378 B2 1/2013 Marczyk et al.
8,342,379 B2 1/2013 Whitman et al.
8,342,380 B2 1/2013 Viola
8,348,123 B2 1/2013 Scirica et al.
8,348,124 B2 1/2013 Scirica
8,348,125 B2 1/2013 Viola et al.
8,348,126 B2 1/2013 Olson et al.
8,348,127 B2 1/2013 Marczyk
8,348,129 B2 1/2013 Bedi et al.
8,348,130 B2 1/2013 Shah et al.
8,348,131 B2 1/2013 Omaits et al.
8,353,437 B2 1/2013 Boudreaux
8,353,440 B2 1/2013 Whitman et al.
8,356,740 B1 1/2013 Knodel
8,357,174 B2 1/2013 Roth et al.
8,360,294 B2 1/2013 Scirica
8,360,297 B2 1/2013 Shelton, IV et al.
8,360,298 B2 1/2013 Farascioni et al.
8,360,299 B2 1/2013 Zemlok et al.
8,365,971 B1 2/2013 Knodel
8,365,972 B2 2/2013 Aranyi et al.
8,365,973 B1 2/2013 White et al.
8,365,976 B2 2/2013 Hess et al.
8,371,491 B2 2/2013 Huitema et al.
8,371,492 B2 2/2013 Aranyi et al.
8,371,493 B2 2/2013 Aranyi et al.
8,381,828 B2 2/2013 Whitman et al.
8,381,961 B2 2/2013 Holsten et al.
8,387,848 B2 3/2013 Johnson et al.
8,387,849 B2 3/2013 Buesseler et al.
8,387,850 B2 3/2013 Hathaway et al.
8,388,652 B2 3/2013 Viola
8,393,513 B2 3/2013 Jankowski
8,393,514 B2 3/2013 Shelton, IV et al.
8,393,516 B2 3/2013 Kostrzewski
8,397,971 B2 3/2013 Yates et al.
8,397,972 B2 3/2013 Kostrzewski
8,403,195 B2 3/2013 Beardsley et al.
8,403,196 B2 3/2013 Beardsley et al.
8,403,197 B2 3/2013 Vidal et al.
8,403,198 B2 3/2013 Sorrentino et al.
8,403,956 B1 3/2013 Thompson et al.
8,408,439 B2 4/2013 Huang et al.
8,408,440 B2 4/2013 Olson et al.
8,408,442 B2 4/2013 Racenet et al.
8,413,868 B2 4/2013 Cappola
8,413,869 B2 4/2013 Heinrich
8,413,871 B2 4/2013 Racenet et al.
8,418,904 B2 4/2013 Wenchell et al.
8,418,905 B2 4/2013 Milliman
8,418,906 B2 4/2013 Farascioni et al.
8,418,907 B2 4/2013 Johnson et al.
8,418,908 B1 4/2013 Beardsley
8,419,768 B2 4/2013 Marczyk
8,424,735 B2 4/2013 Viola et al.
8,424,736 B2 4/2013 Scirica et al.
8,424,737 B2 4/2013 Scirica
8,424,739 B2 4/2013 Racenet et al.
8,424,740 B2 4/2013 Shelton, IV et al.
8,439,244 B2 5/2013 Holcomb et al.
8,439,245 B2 5/2013 Knodel et al.
8,439,246 B1 5/2013 Knodel
8,444,036 B2 5/2013 Shelton, IV
8,444,037 B2 5/2013 Nicholas et al.
8,444,038 B2 5/2013 Farascioni et al.
8,448,832 B2 5/2013 Viola et al.
8,453,652 B2 6/2013 Stopek
8,453,905 B2 6/2013 Holcomb et al.
8,453,906 B2 6/2013 Huang et al.
8,453,907 B2 6/2013 Laurent et al.
8,453,908 B2 6/2013 Bedi et al.
8,453,909 B2 6/2013 Olson et al.
8,453,910 B2 6/2013 Bettuchi et al.
8,453,912 B2 6/2013 Mastri et al.
8,453,913 B2 6/2013 Milliman
8,453,914 B2 6/2013 Laurent et al.
8,454,628 B2 6/2013 Smith et al.
8,459,520 B2 6/2013 Giordano et al.
8,459,521 B2 6/2013 Zemlok et al.
8,459,522 B2 6/2013 Marczyk
8,459,523 B2 6/2013 Whitman
8,459,524 B2 6/2013 Pribanic et al.
8,459,525 B2 6/2013 Yates et al.
8,464,922 B2 6/2013 Marczyk
8,464,923 B2 6/2013 Shelton, IV
8,469,252 B2 6/2013 Holcomb et al.
8,469,254 B2 6/2013 Czernik et al.
8,474,677 B2 7/2013 Woodard, Jr. et al.
8,479,967 B2 7/2013 Marczyk
8,479,968 B2 7/2013 Hodgkinson et al.
8,479,969 B2 7/2013 Shelton, IV
8,485,412 B2 7/2013 Shelton, IV et al.
8,490,852 B2 7/2013 Viola
8,496,152 B2 7/2013 Viola
8,496,154 B2 7/2013 Marczyk et al.
8,496,156 B2 7/2013 Sniffin et al.
8,496,683 B2 7/2013 Prommersberger et al.
8,499,993 B2 8/2013 Shelton, IV et al.
8,505,799 B2 8/2013 Viola et al.
8,505,802 B2 8/2013 Viola et al.
8,511,575 B2 8/2013 Cok
8,512,359 B2 8/2013 Whitman et al.
8,512,402 B2 8/2013 Marczyk et al.
8,517,240 B1 8/2013 Mata et al.
8,517,241 B2 8/2013 Nicholas et al.
8,517,243 B2 8/2013 Giordano et al.
8,517,244 B2 8/2013 Shelton, IV et al.
8,523,041 B2 9/2013 Ishitsuki et al.
8,523,042 B2 9/2013 Masiakos et al.
8,523,043 B2 9/2013 Ullrich et al.
8,534,528 B2 9/2013 Shelton, IV
8,540,128 B2 9/2013 Shelton, IV et al.
8,540,129 B2 9/2013 Baxter, III et al.
8,540,130 B2 9/2013 Moore et al.
8,540,131 B2 9/2013 Swayze
8,540,733 B2 9/2013 Whitman et al.
8,544,711 B2 10/2013 Ma et al.
8,550,325 B2 10/2013 Cohen et al.
8,556,151 B2 10/2013 Viola
8,561,870 B2 10/2013 Baxter, III et al.
8,561,873 B2 10/2013 Ingmanson et al.
8,561,874 B2 10/2013 Scirica
8,567,656 B2 10/2013 Shelton, IV et al.
8,573,461 B2 11/2013 Shelton, IV et al.
8,573,463 B2 11/2013 Scirica et al.
8,573,465 B2 11/2013 Shelton, IV
8,579,176 B2 11/2013 Smith et al.
8,579,177 B2 11/2013 Beetel
8,584,919 B2 11/2013 Hueil et al.
8,584,920 B2 11/2013 Hodgkinson
8,590,762 B2 11/2013 Hess et al.
8,596,515 B2 12/2013 Okoniewski
8,597,311 B2 12/2013 Criscuolo et al.
8,602,288 B2 12/2013 Shelton, IV et al.
8,608,045 B2 12/2013 Smith et al.
8,608,046 B2 12/2013 Laurent et al.
8,608,047 B2 12/2013 Holsten et al.
8,613,383 B2 12/2013 Beckman et al.
8,613,384 B2 12/2013 Pastorelli et al.
8,616,427 B2 12/2013 Viola
8,616,430 B2 12/2013 (Prommersberger) Stopek et al.
8,627,994 B2 1/2014 Zemlok et al.
8,628,544 B2 1/2014 Farascioni
8,631,988 B2 1/2014 Viola
8,631,989 B2 1/2014 Aranyi et al.
8,631,991 B2 1/2014 Cropper et al.
8,632,525 B2 1/2014 Kerr et al.

(56) References Cited

U.S. PATENT DOCUMENTS 8,632,535 B2 1/2014 Shelton, IV et al.
8,636,187 B2 1/2014 Hueil et al.
8,636,190 B2 1/2014 Zemlok et al.
8,636,192 B2 1/2014 Farascioni et al.
8,636,762 B2 1/2014 Whitman et al.
8,636,766 B2 1/2014 Milliman et al.
8,640,940 B2 2/2014 Ohdaira
8,657,174 B2 2/2014 Yates et al.
8,657,177 B2 2/2014 Scirica et al.
8,657,178 B2 2/2014 Hueil et al.
8,662,371 B2 3/2014 Viola
8,668,129 B2 3/2014 Olson
8,672,206 B2 3/2014 Aranyi et al.
8,672,208 B2 3/2014 Hess et al.
8,672,209 B2 3/2014 Crainich
8,678,263 B2 3/2014 Viola
8,678,990 B2 3/2014 Wazer et al.
8,679,155 B2 3/2014 Knodel et al.
8,684,247 B2 4/2014 Scirica et al.
8,684,249 B2 4/2014 Racenet et al.
8,684,253 B2 4/2014 Giordano et al.
8,690,039 B2 4/2014 Beardsley et al.
8,695,865 B2 4/2014 Smith et al.
8,695,866 B2 4/2014 Leimbach et al.
8,701,958 B2 4/2014 Shelton, IV et al.
8,701,959 B2 4/2014 Shah
8,701,961 B2 4/2014 Ivanko
8,708,213 B2 4/2014 Shelton, IV et al.
8,714,429 B2 5/2014 Demmy
8,715,277 B2 5/2014 Weizman
8,720,766 B2 5/2014 Hess et al.
8,721,630 B2 5/2014 Ortiz et al.
8,727,197 B2 5/2014 Hess et al.
8,727,200 B2 5/2014 Roy
8,733,612 B2 5/2014 Ma
8,740,034 B2 6/2014 Morgan et al.
8,740,039 B2 6/2014 Farascioni
8,746,529 B2 6/2014 Shelton, IV et al.
8,746,530 B2 6/2014 Giordano et al.
8,746,533 B2 6/2014 Whitman
8,746,534 B2 6/2014 Farascioni
8,746,535 B2 6/2014 Shelton, IV et al.
8,747,421 B2 6/2014 Balbierz et al.
8,752,747 B2 6/2014 Shelton, IV et al.
8,752,748 B2 6/2014 Whitman et al.
8,752,749 B2 6/2014 Moore et al.
8,757,465 B2 6/2014 Woodard, Jr. et al.
8,758,391 B2 6/2014 Swayze et al.
8,763,875 B2 7/2014 Morgan et al.
8,763,876 B2 7/2014 Kostrzewski
8,763,877 B2 7/2014 Schall et al.
8,763,879 B2 7/2014 Shelton, IV et al.
8,770,458 B2 7/2014 Scirica
8,777,082 B2 7/2014 Scirica
8,783,541 B2 7/2014 Shelton, IV et al.
8,783,542 B2 7/2014 Riestenberg et al.
8,789,737 B2 7/2014 Hodgkinson et al.
8,789,738 B2 7/2014 Knodel et al.
8,789,739 B2 7/2014 Swensgard
8,800,838 B2 8/2014 Shelton, IV
8,800,840 B2 8/2014 Jankowski
8,800,841 B2 8/2014 Ellerhorst et al.
8,808,311 B2 8/2014 Heinrich et al.
8,814,024 B2 8/2014 Woodard, Jr. et al.
8,814,025 B2 8/2014 Miller et al.
8,820,603 B2 9/2014 Shelton, IV et al.
8,820,605 B2 9/2014 Shelton, IV
8,820,606 B2 9/2014 Hodgkinson
8,820,607 B2 9/2014 Marczyk
8,827,133 B2 9/2014 Shelton, IV et al.
8,827,134 B2 9/2014 Viola et al.
8,833,631 B2 9/2014 Munro et al.
8,833,632 B2 9/2014 Swensgard
8,840,003 B2 9/2014 Morgan et al.
8,840,603 B2 9/2014 Shelton, IV et al.
8,844,788 B2 9/2014 Knodel
8,851,354 B2 10/2014 Swensgard et al.
8,851,355 B2 10/2014 Aranyi et al.
8,857,693 B2 10/2014 Schuckmann et al.
8,864,007 B2 10/2014 Widenhouse et al.
8,864,009 B2 10/2014 Shelton, IV et al.
8,864,010 B2 10/2014 Williams
8,870,050 B2 10/2014 Hodgkinson
8,875,971 B2 11/2014 Hall et al.
8,875,972 B2 11/2014 Weisenburgh, II et al.
8,893,949 B2 11/2014 Shelton, IV et al.
8,893,950 B2 11/2014 Marczyk
8,899,461 B2 12/2014 Farascioni
8,899,462 B2 12/2014 Kostrzewski et al.
8,899,463 B2 12/2014 Schall et al.
8,899,464 B2 12/2014 Hueil et al.
8,900,616 B2 12/2014 Belcheva et al.
8,920,435 B2 12/2014 Smith et al.
8,925,782 B2 1/2015 Shelton, IV
8,926,598 B2 1/2015 Mollere et al.
8,931,681 B2 1/2015 Kostrzewski
8,931,682 B2 1/2015 Timm et al.
8,931,693 B1 1/2015 Kumar et al.
8,955,732 B2 2/2015 Zemlok et al.
8,958,429 B2 2/2015 Shukla et al.
8,960,517 B2 2/2015 Lee
8,960,520 B2 2/2015 McCuen
8,967,443 B2 3/2015 McCuen
8,967,446 B2 3/2015 Beardsley et al.
8,973,803 B2 3/2015 Hall et al.
8,978,954 B2 3/2015 Shelton, IV et al.
8,978,956 B2 3/2015 Schall et al.
8,991,677 B2 3/2015 Moore et al.
8,991,678 B2 3/2015 Wellman et al.
8,998,058 B2 4/2015 Moore et al.
8,998,060 B2 4/2015 Bruewer et al.
9,005,230 B2 4/2015 Yates et al.
9,010,606 B2 4/2015 Aranyi et al.
9,010,607 B2 4/2015 Kostrzewski
9,010,610 B2 4/2015 Hodgkinson
9,016,539 B2 4/2015 Kostrzewski et al.
9,016,541 B2 4/2015 Viola et al.
9,016,542 B2 4/2015 Shelton, IV et al.
9,016,544 B2 4/2015 Hodgkinson et al.
9,016,545 B2 4/2015 Aranyi et al.
9,016,546 B2 4/2015 Demmy et al.
9,017,371 B2 4/2015 Whitman et al.
9,022,271 B2 5/2015 Scirica
9,027,817 B2 5/2015 Milliman et al.
9,033,203 B2 5/2015 Woodard, Jr. et al.
9,044,228 B2 6/2015 Woodard, Jr. et al.
9,044,229 B2 6/2015 Scheib et al.
9,050,084 B2 6/2015 Schmid et al.
9,055,941 B2 6/2015 Schmid et al.
9,060,770 B2 6/2015 Shelton, IV et al.
9,072,535 B2 7/2015 Shelton, IV et al.
9,084,601 B2 7/2015 Moore et al.
9,084,602 B2 7/2015 Gleiman
9,089,326 B2 7/2015 Krumanaker et al.
9,095,339 B2 8/2015 Moore et al.
9,101,359 B2 8/2015 Smith et al.
9,107,663 B2 8/2015 Swensgard
9,107,664 B2 8/2015 Marczyk
9,107,667 B2 8/2015 Hodgkinson
9,113,862 B2 8/2015 Morgan et al.
9,113,864 B2 8/2015 Morgan et al.
9,113,870 B2 8/2015 Viola
9,113,872 B2 8/2015 Viola
9,113,880 B2 8/2015 Zemlok et al.
9,125,649 B2 9/2015 Bruewer et al.
9,138,225 B2 9/2015 Huang et al.
9,155,537 B2 10/2015 Katre et al.
9,179,912 B2 11/2015 Yates et al.
9,192,378 B2 11/2015 Aranyi et al.
9,192,379 B2 11/2015 Aranyi et al.
9,192,384 B2 11/2015 Bettuchi
9,198,644 B2 12/2015 Balek et al.
9,198,660 B2 12/2015 Hodgkinson
9,198,661 B2 12/2015 Swensgard

(56) References Cited

U.S. PATENT DOCUMENTS 9,198,662 B2 12/2015 Barton et al.
9,204,876 B2 12/2015 Cappola et al.
9,204,877 B2 12/2015 Whitman et al.
9,204,880 B2 12/2015 Baxter, III et al.
9,216,019 B2 12/2015 Schmid et al.
9,216,020 B2 12/2015 Zhang et al.
9,220,500 B2 12/2015 Swayze et al.
9,220,501 B2 12/2015 Baxter, III et al.
9,220,502 B2 12/2015 Zemlok et al.
9,232,941 B2 1/2016 Mandakolathur Vasudevan et al.
9,232,944 B2 1/2016 Cappola et al.
9,237,891 B2 1/2016 Shelton, IV
9,237,892 B2 1/2016 Hodgkinson
9,254,180 B2 2/2016 Huitema et al.
9,265,585 B2 2/2016 Wingardner et al.
9,271,728 B2 3/2016 Gupta et al.
9,272,406 B2 3/2016 Aronhalt et al.
9,277,919 B2 3/2016 Timmer et al.
9,282,962 B2 3/2016 Schmid et al.
9,283,054 B2 3/2016 Morgan et al.
9,289,209 B2 3/2016 Gurumurthy et al.
9,289,210 B2 3/2016 Baxter, III et al.
9,289,225 B2 3/2016 Shelton, IV et al.
9,295,464 B2 3/2016 Shelton, IV et al.
9,295,465 B2 3/2016 Farascioni
9,295,466 B2 3/2016 Hodgkinson et al.
9,301,752 B2 4/2016 Mandakolathur Vasudevan et al.
9,301,753 B2 4/2016 Aldridge et al.
9,301,757 B2 4/2016 Williams
9,301,759 B2 4/2016 Spivey et al.
9,307,965 B2 4/2016 Ming et al.
9,307,986 B2 4/2016 Hall et al.
9,307,989 B2 4/2016 Shelton, IV et al.
9,314,246 B2 4/2016 Shelton, IV et al.
9,320,518 B2 4/2016 Henderson et al.
9,320,521 B2 4/2016 Shelton, IV et al.
9,320,523 B2 4/2016 Shelton, IV et al.
9,326,767 B2 5/2016 Koch, Jr. et al.
9,326,771 B2 5/2016 Baxter, III et al.
9,332,987 B2 5/2016 Leimbach et al.
9,345,477 B2 5/2016 Anim et al.
9,345,478 B2 5/2016 Knodel
9,345,479 B2 5/2016 (Tarinelli) Racenet et al.
9,345,481 B2 5/2016 Hall et al.
9,345,780 B2 5/2016 Manoharan et al.
9,351,726 B2 5/2016 Leimbach
9,351,727 B2 5/2016 Leimbach et al.
9,351,732 B2 5/2016 Hodgkinson
9,358,003 B2 6/2016 Hall et al.
9,364,217 B2 6/2016 Kostrzewski et al.
9,364,218 B2 6/2016 Scirica
9,364,219 B2 6/2016 Olson et al.
9,364,220 B2 6/2016 Williams
9,364,227 B2 6/2016 Kostrzewski
9,364,231 B2 6/2016 Wenchell
9,364,233 B2 6/2016 Alexander, III et al.
9,370,358 B2 6/2016 Shelton, IV et al.
9,370,362 B2 6/2016 Petty et al.
9,386,983 B2 7/2016 Swensgard et al.
9,386,984 B2 7/2016 Aronhalt et al.
9,386,988 B2 7/2016 Baxter, III et al.
9,393,018 B2 7/2016 Wang et al.
9,398,911 B2 7/2016 Auld
9,402,604 B2 8/2016 Williams et al.
9,402,627 B2 8/2016 Stevenson et al.
9,421,014 B2 8/2016 Ingmanson et al.
9,433,419 B2 9/2016 Gonzalez et al.
9,433,420 B2 9/2016 Hodgkinson
9,445,810 B2 9/2016 Cappola
9,445,813 B2 9/2016 Shelton, IV et al.
9,451,959 B2 9/2016 Patankar et al.
9,468,438 B2 10/2016 Baber et al.
9,468,439 B2 10/2016 Cappola et al.
9,480,476 B2 11/2016 Aldridge et al.
9,480,492 B2 11/2016 Aranyi et al.
9,492,171 B2 11/2016 Patenaude
9,498,212 B2 11/2016 Racenet et al.
9,498,219 B2 11/2016 Moore et al.
9,510,827 B2 12/2016 Kostrzewski
9,517,065 B2 12/2016 Simms et al.
9,517,066 B2 12/2016 Racenet et al.
9,522,002 B2 12/2016 Chowaniec et al.
9,539,007 B2 1/2017 Dhakad et al.
9,549,735 B2 1/2017 Shelton, IV et al.
9,554,794 B2 1/2017 Baber
9,561,029 B2 2/2017 Scheib et al.
9,561,031 B2 2/2017 Heinrich et al.
9,566,065 B2 2/2017 Knodel
9,572,576 B2 2/2017 Hodgkinson et al.
9,579,101 B2 2/2017 Whitman et al.
9,585,657 B2 3/2017 Shelton, IV et al.
9,585,662 B2 3/2017 Shelton, IV et al.
9,597,077 B2 3/2017 Hodgkinson
9,610,080 B2 4/2017 Whitfield et al.
9,615,825 B2 4/2017 Viola
9,615,826 B2 4/2017 Shelton, IV et al.
9,622,746 B2 4/2017 Simms
9,629,623 B2 4/2017 Lytle, IV et al.
9,629,626 B2 4/2017 Soltz et al.
9,629,628 B2 4/2017 Aranyi
9,629,629 B2 4/2017 Leimbach et al.
9,642,620 B2 5/2017 Baxter, III
9,649,109 B2 5/2017 Ranucci et al.
9,655,613 B2 5/2017 Schaller
9,662,108 B2 5/2017 Williams
9,668,728 B2 6/2017 Williams et al.
9,668,732 B2 6/2017 Patel et al.
9,675,351 B2 6/2017 Hodgkinson et al.
9,681,870 B2 6/2017 Baxter, III et al.
9,687,230 B2 6/2017 Leimbach et al.
9,687,233 B2 6/2017 Fernandez et al.
9,693,772 B2 7/2017 Ingmanson et al.
9,700,309 B2 7/2017 Jaworek
9,700,319 B2 7/2017 Motooka et al.
9,706,993 B2 7/2017 Hessler et al.
9,713,474 B2 7/2017 Lorenz
9,717,497 B2 8/2017 Zerkle et al.
9,717,498 B2 8/2017 Aranyi et al.
9,724,092 B2 8/2017 Baxter, III et al.
9,724,095 B2 8/2017 Gupta et al.
9,763,662 B2 9/2017 Shelton, IV et al.
9,770,245 B2 9/2017 Swayze et al.
9,775,610 B2 10/2017 Nicholas et al.
9,775,635 B2 10/2017 Takei
9,782,169 B2 10/2017 Kimsey
9,782,173 B2 10/2017 Mozdzierz
9,795,379 B2 10/2017 Leimbach et al.
9,795,384 B2 10/2017 Weaner et al.
9,808,246 B2 11/2017 Shelton, IV
9,808,248 B2 11/2017 Hoffman
9,808,249 B2 11/2017 Shelton, IV
9,820,741 B2 11/2017 Kostrzewski
9,820,742 B2 11/2017 Covach et al.
9,827,002 B2 11/2017 Hausen et al.
9,839,420 B2 12/2017 Shelton, IV
9,839,421 B2 12/2017 Zerkle et al.
9,839,428 B2 12/2017 Baxter, III et al.
9,855,038 B2 1/2018 Smith et al.
9,855,040 B2 1/2018 Kostrzewski
9,861,358 B2 1/2018 Marczyk et al.
9,861,359 B2 1/2018 Shelton, IV et al.
9,867,612 B2 1/2018 Parihar et al.
9,867,613 B2 1/2018 Marczyk et al.
9,867,615 B2 1/2018 Fanelli et al.
9,872,683 B2 1/2018 Hopkins
9,883,860 B2 2/2018 Leimbach et al.
9,901,342 B2 2/2018 Shelton, IV et al.
9,913,646 B2 3/2018 Shelton, IV
9,918,714 B2 3/2018 Gibbons, Jr.
9,918,717 B2 3/2018 Czernik
9,924,941 B2 3/2018 Burbank
9,924,942 B2 3/2018 Swayze et al.
9,936,951 B2 4/2018 Hufnagel et al.
9,936,954 B2 4/2018 Shelton, IV et al.

(56) References Cited

U.S. PATENT DOCUMENTS 9,943,311 B2 4/2018 Scirica et al.
9,949,737 B2 4/2018 Zergiebel et al.
9,955,966 B2 5/2018 Zergiebel
9,968,354 B2 5/2018 Shelton, IV et al.
9,980,724 B2 5/2018 Farascioni et al.
9,987,012 B2 6/2018 Shah
9,987,099 B2 6/2018 Chen et al.
9,993,248 B2 6/2018 Shelton, IV et al.
9,993,258 B2 6/2018 Shelton, IV et al.
10,004,497 B2 6/2018 Overmyer et al.
10,004,505 B2 6/2018 Moore et al.
10,034,668 B2 7/2018 Ebner
10,039,532 B2 8/2018 Srinivas et al.
10,039,545 B2 8/2018 Sadowski et al.
10,045,782 B2 8/2018 Murthy Aravalli
10,052,044 B2 8/2018 Shelton, IV et al.
10,058,963 B2 8/2018 Shelton, IV et al.
10,064,622 B2 9/2018 Murthy Aravalli
10,076,325 B2 9/2018 Huang et al.
10,085,750 B2 10/2018 Zergiebel et al.
10,092,290 B2 10/2018 Mgit et al.
10,092,292 B2 10/2018 Boudreaux et al.
10,111,657 B2 10/2018 McCuen
10,111,665 B2 10/2018 Aranyi
10,117,650 B2 11/2018 Nicholas et al.
10,117,654 B2 11/2018 Ingmanson et al.
10,123,796 B2 11/2018 Westling et al.
10,123,798 B2 11/2018 Baxter, III et al.
10,135,242 B2 11/2018 Baber et al.
10,143,474 B2 12/2018 Bucciaglia et al.
10,172,612 B2 1/2019 Frushour
10,172,615 B2 1/2019 Marczyk et al.
10,172,617 B2 1/2019 Shelton, IV et al.
10,175,127 B2 1/2019 Collins et al.
10,180,463 B2 1/2019 Beckman et al.
10,182,816 B2 1/2019 Shelton, IV et al.
10,206,677 B2 2/2019 Harris et al.
10,213,201 B2 2/2019 Shelton, IV et al.
10,219,804 B2 3/2019 Linder et al.
10,226,239 B2 3/2019 Nicholas et al.
10,226,250 B2 3/2019 Beckman et al.
10,226,254 B2 3/2019 Cabrera et al.
10,245,033 B2 4/2019 Overmyer et al.
10,245,038 B2 4/2019 Hopkins et al.
10,251,725 B2 4/2019 Valentine et al.
10,265,065 B2 4/2019 Shelton, IV et al.
10,265,066 B2 4/2019 Measamer et al.
10,265,074 B2 4/2019 Shelton, IV et al.
10,271,840 B2 4/2019 Sapre
10,271,841 B2 4/2019 Overmyer et al.
10,285,694 B2 5/2019 Viola et al.
10,285,698 B2 5/2019 Cappola et al.
10,321,907 B2 6/2019 Shelton, IV et al.
10,327,776 B2 6/2019 Harris et al.
10,335,150 B2 7/2019 Shelton, IV
10,349,939 B2 7/2019 Shelton, IV et al.
10,349,941 B2 7/2019 Marczyk et al.
10,390,823 B2 8/2019 Shelton, IV et al.
10,390,825 B2 8/2019 Shelton, IV et al.
10,390,828 B2 8/2019 Vendely et al.
10,405,857 B2 9/2019 Shelton
10,426,468 B2 10/2019 Contini et al.
10,441,279 B2 10/2019 Shelton, IV et al.
10,456,129 B2 10/2019 Shelton, IV et al.
10,456,130 B2 10/2019 Cheney et al.
10,463,368 B2 11/2019 Kostrzewski
10,470,762 B2 11/2019 Leimbach et al.
10,470,911 B2 11/2019 Thompson et al.
10,478,182 B2 11/2019 Taylor
10,478,183 B2 11/2019 Hess et al.
10,478,187 B2 11/2019 Shelton, IV et al.
10,542,976 B2 1/2020 Calderoni et al.
10,548,504 B2 2/2020 Shelton, IV et al.
10,548,593 B2 2/2020 Shelton, IV et al.
10,548,599 B2 2/2020 Marczyk et al.
10,561,417 B2 2/2020 Zergiebel et al.
10,561,418 B2 2/2020 Richard et al.
10,568,621 B2 2/2020 Shelton, IV et al.
10,588,629 B2 3/2020 Malinouskas et al.
10,595,929 B2 3/2020 Boudreaux et al.
10,603,128 B2 3/2020 Zergiebel et al.
10,617,412 B2 4/2020 Shelton, IV et al.
10,624,634 B2 4/2020 Shelton, IV et al.
10,687,806 B2 6/2020 Shelton, IV et al.
10,695,053 B2 6/2020 Hess et al.
10,779,822 B2 9/2020 Yates et al.
10,792,038 B2 10/2020 Becerra et al.
10,828,030 B2 11/2020 Weir et al.
10,863,984 B2 12/2020 Shelton, IV et al.
10,987,104 B2 * 4/2021 Beardsley ............ A61B 17/072
12,193,666 B2 * 1/2025 Whitfield ......... A61B 17/07207
2004/0108357 A1 6/2004 Milliman et al.
2004/0199180 A1 10/2004 Knodel et al.
2004/0199181 A1 10/2004 Knodel et al.
2004/0243151 A1 12/2004 Demmy et al.
2004/0267310 A1 12/2004 Racenet et al.
2005/0216055 A1 9/2005 Scirica et al.
2006/0049229 A1 3/2006 Milliman et al.
2006/0180634 A1 8/2006 Shelton et al.
2006/0289602 A1 12/2006 Wales et al.
2007/0073341 A1 3/2007 Smith et al.
2007/0084897 A1 4/2007 Shelton et al.
2007/0102472 A1 5/2007 Shelton
2007/0106317 A1 5/2007 Shelton et al.
2007/0119901 A1 5/2007 Ehrenfels et al.
2007/0145096 A1 6/2007 Viola et al.
2007/0170225 A1 7/2007 Shelton et al.
2007/0175950 A1 8/2007 Shelton et al.
2007/0175951 A1 8/2007 Shelton et al.
2007/0175955 A1 8/2007 Shelton et al.
2007/0194079 A1 8/2007 Hueil et al.
2007/0194082 A1 8/2007 Morgan et al.
2008/0029570 A1 2/2008 Shelton et al.
2008/0029573 A1 2/2008 Shelton et al.
2008/0029574 A1 2/2008 Shelton et al.
2008/0029575 A1 2/2008 Shelton et al.
2008/0078802 A1 4/2008 Hess et al.
2008/0110961 A1 5/2008 Voegele et al.
2008/0169328 A1 7/2008 Shelton
2008/0169332 A1 7/2008 Shelton et al.
2008/0169333 A1 7/2008 Shelton et al.
2008/0287987 A1 11/2008 Boyden et al.
2008/0296346 A1 12/2008 Shelton, IV et al.
2008/0308602 A1 12/2008 Timm et al.
2008/0308603 A1 12/2008 Shelton et al.
2008/0308608 A1 12/2008 Prommersberger
2009/0001121 A1 1/2009 Hess et al.
2009/0001130 A1 1/2009 Hess et al.
2009/0090763 A1 4/2009 Zemlok et al.
2009/0090766 A1 4/2009 Knodel
2009/0242610 A1 10/2009 Shelton, IV et al.
2009/0255974 A1 10/2009 Viola
2009/0308907 A1 12/2009 Nalagatla et al.
2010/0012703 A1 1/2010 Calabrese et al.
2010/0065604 A1 3/2010 Weng
2010/0069942 A1 3/2010 Shelton, IV
2010/0127041 A1 5/2010 Morgan et al.
2010/0133317 A1 6/2010 Shelton, IV et al.
2010/0147921 A1 6/2010 Olson
2010/0147922 A1 6/2010 Olson
2010/0155453 A1 6/2010 Bombard et al.
2010/0193566 A1 8/2010 Scheib et al.
2010/0224668 A1 9/2010 Fontayne et al.
2010/0249802 A1 9/2010 May et al.
2010/0252611 A1 10/2010 Ezzat et al.
2011/0006101 A1 1/2011 Hall et al.
2011/0024477 A1 2/2011 Hall
2011/0024478 A1 2/2011 Shelton, IV
2011/0036891 A1 2/2011 Zemlok et al.
2011/0087276 A1 4/2011 Bedi et al.
2011/0101069 A1 5/2011 Bombard et al.
2011/0147433 A1 6/2011 Shelton, IV et al.
2011/0163146 A1 7/2011 Ortiz et al.
2011/0192882 A1 8/2011 Hess et al.

(56) References Cited

U.S. PATENT DOCUMENTS

2011/0278343 A1 11/2011 Knodel et al.
2011/0290856 A1 12/2011 Shelton, IV et al.
2012/0053406 A1 3/2012 Conlon et al.
2012/0061446 A1 3/2012 Knodel et al.
2012/0074200 A1 3/2012 Schmid et al.
2012/0080478 A1 4/2012 Morgan et al.
2012/0080495 A1 4/2012 Holcomb et al.
2012/0080498 A1 4/2012 Shelton, IV et al.
2012/0091183 A1 4/2012 Manoux et al.
2012/0138659 A1 6/2012 Marczyk et al.
2012/0193394 A1 8/2012 Holcomb et al.
2012/0193399 A1 8/2012 Holcomb et al.
2012/0211542 A1 8/2012 Racenet
2012/0228358 A1 9/2012 Zemlok et al.
2012/0234895 A1 9/2012 O'Connor et al.
2012/0234897 A1 9/2012 Shelton, IV et al.
2012/0241504 A1 9/2012 Soltz et al.
2012/0248169 A1 10/2012 Widenhouse et al.
2012/0286022 A1 11/2012 Olson et al.
2012/0298722 A1 11/2012 Hess et al.
2013/0008937 A1 1/2013 Viola
2013/0012983 A1 1/2013 Kleyman
2013/0020375 A1 1/2013 Shelton, IV et al.
2013/0020376 A1 1/2013 Shelton, IV et al.
2013/0026208 A1 1/2013 Shelton, IV et al.
2013/0026210 A1 1/2013 Shelton, IV et al.
2013/0041406 A1 2/2013 Bear et al.
2013/0068816 A1 3/2013 Mandakolathur Vasudevan et al.
2013/0068818 A1 3/2013 Kasvikis
2013/0075447 A1 3/2013 Weisenburgh, II et al.
2013/0098966 A1* 4/2013 Kostrzewski .... A61B 17/07207 606/1
2013/0098970 A1 4/2013 Racenet et al.
2013/0153641 A1 6/2013 Shelton, IV et al.
2013/0175316 A1 7/2013 Thompson et al.
2013/0256380 A1 10/2013 Schmid et al.
2013/0277410 A1 10/2013 Fernandez et al.
2013/0313305 A1* 11/2013 Scirica ............ A61B 17/07207 227/180.1
2013/0334280 A1 12/2013 Krehel et al.
2014/0014704 A1 1/2014 Onukuri et al.
2014/0014707 A1 1/2014 Onukuri et al.
2014/0048580 A1 2/2014 Merchant et al.
2014/0166724 A1 6/2014 Schellin et al.
2014/0166725 A1 6/2014 Schellin et al.
2014/0166726 A1 6/2014 Schellin et al.
2014/0175150 A1 6/2014 Shelton, IV et al.
2014/0239047 A1 8/2014 Hodgkinson et al.
2014/0246475 A1 9/2014 Hall et al.
2014/0252064 A1 9/2014 Mozdzierz et al.
2014/0263541 A1 9/2014 Leimbach et al.
2014/0263552 A1 9/2014 Hall et al.
2014/0263558 A1 9/2014 Hausen et al.
2014/0284371 A1 9/2014 Morgan et al.
2014/0291379 A1 10/2014 Schellin et al.
2014/0291383 A1 10/2014 Spivey et al.
2014/0367445 A1 12/2014 Ingmanson et al.
2015/0076211 A1 3/2015 Irka et al.
2015/0134076 A1 5/2015 Shelton, IV et al.
2015/0173749 A1 6/2015 Shelton, IV et al.
2015/0173756 A1 6/2015 Baxter, III et al.
2015/0250474 A1 9/2015 Abbott et al.
2015/0272557 A1 10/2015 Overmyer et al.
2015/0297222 A1 10/2015 Huitema et al.
2015/0297225 A1 10/2015 Huitema et al.
2015/0374364 A1 12/2015 Gettinger et al.
2015/0374372 A1 12/2015 Zergiebel et al.
2016/0066909 A1 3/2016 Baber et al.
2016/0166249 A1 6/2016 Knodel
2016/0166253 A1 6/2016 Knodel
2016/0235494 A1 8/2016 Shelton, IV et al.
2016/0302791 A1 10/2016 Schmitt
2016/0354176 A1 12/2016 Schmitt
2017/0000483 A1 1/2017 Motai et al.
2017/0112561 A1 4/2017 Motai
2017/0290584 A1 10/2017 Jasemian et al.
2017/0296172 A1 10/2017 Harris et al.
2017/0303924 A1 10/2017 Scheib
2018/0008260 A1 1/2018 Baxter, III et al.
2018/0168637 A1 6/2018 Harris
2018/0168644 A1 6/2018 Shelton, IV et al.
2018/0168649 A1 6/2018 Shelton, IV et al.
2018/0168651 A1 6/2018 Shelton, IV et al.
2018/0235610 A1 8/2018 Harris et al.
2018/0325514 A1 11/2018 Harris et al.
2018/0344318 A1* 12/2018 Nicholas .......... A61B 17/07207
2019/0099181 A1 4/2019 Shelton, IV et al.
2019/0099182 A1 4/2019 Bakos et al.
2019/0150919 A1 5/2019 Williams et al.
2019/0261984 A1 8/2019 Nelson et al.
2019/0298341 A1 10/2019 Shelton, IV et al.
2019/0298350 A1 10/2019 Shelton, IV et al.
2019/0298351 A1 10/2019 Shelton, IV et al.
2019/0314016 A1 10/2019 Huitema et al.
2019/0314019 A1 10/2019 Rector et al.
2020/0054323 A1 2/2020 Harris et al.
2020/0121317 A1 4/2020 Kostrzewski
2020/0237368 A1 7/2020 Bruns et al.
2021/0077102 A1 3/2021 Williams
2023/0404576 A1 12/2023 Whitfield et al.

FOREIGN PATENT DOCUMENTS

CA 2884962 A1 11/2015
DE 2744824 A1 4/1978
DE 2903159 A1 7/1980
DE 3114135 A1 10/1982
DE 4213426 A1 10/1992
DE 4300307 A1 7/1994
EP 0041022 A1 12/1981
EP 0136950 A2 4/1985
EP 0140552 A2 5/1985
EP 0156774 A2 10/1985
EP 0213817 A1 3/1987
EP 0216532 A1 4/1987
EP 0220029 A1 4/1987
EP 0273468 A2 7/1988
EP 0324166 A2 7/1989
EP 0324635 A1 7/1989
EP 0324637 A1 7/1989
EP 0324638 A1 7/1989
EP 0365153 A1 4/1990
EP 0369324 A1 5/1990
EP 0373762 A1 6/1990
EP 0380025 A2 8/1990
EP 0399701 A1 11/1990
EP 0449394 A2 10/1991
EP 0484677 A1 5/1992
EP 0489436 A1 6/1992
EP 0503662 A1 9/1992
EP 0514139 A2 11/1992
EP 0536903 A2 4/1993
EP 0537572 A2 4/1993
EP 0539762 A1 5/1993
EP 0541950 A1 5/1993
EP 0545029 A1 6/1993
EP 0552050 A2 7/1993
EP 0552423 A2 7/1993
EP 0579038 A1 1/1994
EP 0589306 A2 3/1994
EP 0591946 A1 4/1994
EP 0592243 A2 4/1994
EP 0593920 A1 4/1994
EP 0598202 A1 5/1994
EP 0598579 A1 5/1994
EP 0600182 A2 6/1994
EP 0621006 A1 10/1994
EP 0621009 A1 10/1994
EP 0656188 A2 6/1995
EP 0666057 A2 8/1995
EP 0705571 A1 4/1996
EP 0760230 A1 3/1997
EP 1952769 A2 8/2008
EP 2090253 A2 8/2009

(56) References Cited

FOREIGN PATENT DOCUMENTS

| | | | |
|---|---|---|---|
| EP | 2090254 | A1 | 8/2009 |
| EP | 2583630 | A2 | 4/2013 |
| EP | 2586382 | A2 | 5/2013 |
| EP | 2907456 | A1 | 8/2015 |
| EP | 3138509 | A1 | 3/2017 |
| EP | 3338660 | A1 | 6/2018 |
| EP | 3858259 | A1 | 8/2021 |
| FR | 391239 | A | 10/1908 |
| FR | 2542188 | A1 | 9/1984 |
| FR | 2660851 | A1 | 10/1991 |
| FR | 2681775 | A1 | 4/1993 |
| GB | 1352554 | A | 5/1974 |
| GB | 1452185 | A | 10/1976 |
| GB | 1555455 | A | 11/1979 |
| GB | 2048685 | A | 12/1980 |
| GB | 2070499 | A | 9/1981 |
| GB | 2141066 | A | 12/1984 |
| GB | 2165559 | A | 4/1986 |
| JP | 51149985 | | 12/1976 |
| JP | 2001087272 | | 4/2001 |
| JP | 2013215572 | A | 10/2013 |
| SU | 659146 | A1 | 4/1979 |
| SU | 728848 | A1 | 4/1980 |
| SU | 980703 | A1 | 12/1982 |
| SU | 990220 | A1 | 1/1983 |
| WO | 2008302247 | | 7/1983 |
| WO | 8910094 | A1 | 11/1989 |
| WO | 9210976 | A1 | 7/1992 |
| WO | 9308754 | A1 | 5/1993 |
| WO | 9314706 | A1 | 8/1993 |
| WO | 2004032760 | A2 | 4/2004 |
| WO | 2009071070 | A2 | 6/2009 |
| WO | 2015191887 | A1 | 12/2015 |
| WO | 2018161313 | A1 | 9/2018 |
| WO | 2019186434 | A1 | 10/2019 |

* cited by examiner 16
32
40
34
42

16
42
14
32
44
44
48
40
34
49
46

66
78
88a
88
92
80
94
85
80b
80a
86
90
76
82
84
84

66
78
88
88a
85
82
84
84
7
7
96
76

78
80
66
85
84
82
76
86

REPLACEABLE STAPLE CARTRIDGE WITH RETRACTABLE KNIFE

CROSS-REFERENCE TO RELATED APPLICATIONS

This application is a continuation of U.S. patent application Ser. No. 17/826,271 filed May 27, 2022, entitled "Replaceable Staple Cartridge with Retractable Knife," which is incorporated herein by reference in its entirety.

FIELD

This disclosure is generally related to surgical stapling devices, and more particularly, to surgical stapling devices having replaceable staple cartridges including retractable knives.

BACKGROUND

Surgical stapling devices configured for endoscopic use are well known and commonly used during surgical procedures to minimize patient trauma and reduce patient recovery times. Typically, endoscopic surgical stapling devices include a tool assembly and a drive assembly that is movable in relation to the tool assembly to actuate the tool assembly. The drive assembly includes a knife bar having a cutting blade for cutting tissue. The tool assembly includes anvil and cartridge assemblies that are coupled to each other by a pivot member and movable in relation to each other between open and clamped positions in response to movement of the drive assembly. The cartridge assembly includes a staple cartridge that has an actuation sled, pushers, and staples. Typically, the drive assembly is movable from a retracted position to an advanced position to advance the actuation sled into contact with the pushers and eject the staples from the staple cartridge.

Some stapling devices include a staple cartridge that can be replaced after each firing of the stapling device to facilitate reuse of the stapling device. In such devices, a knife is typically included on the drive assembly and is reused. Other stapling devices include a reload assembly that includes a staple cartridge and a drive assembly that can be replaced after each firing of the stapling device to facilitate reuse of the stapling device. The use of a reload assembly provides a new cutting blade for each firing of the stapling device to maintain the quality of cutting. However, replacement of the drive assembly after each firing of the stapling device is costly.

A continuing need exists for a surgical stapling device that can in a cost-effective manner provide a sharpened cutting blade through multiple firings of the stapling device.

SUMMARY

This disclosure is directed to a surgical stapling device that includes a cartridge assembly having a staple cartridge that is replaceable to facilitate reuse of the stapling device. The staple cartridge includes an actuation sled assembly having an actuation sled, a knife bar, and a retractor link. The retractor link is secured to the knife bar such that the actuation sled assembly is movable through a cartridge body of the staple cartridge. The retractor link is movable from a non-deformed condition disengaged from the drive assembly to a deformed condition engaged with the drive assembly to facilitate retraction of the actuation sled assembly or the knife bar after the stapling device is fired.

Aspects of this disclosure are directed to an actuation sled assembly that includes an actuation sled, a knife bar, and a retractor link. The actuation sled includes a central portion and spaced wedge members positioned on opposite sides of the central portion. The knife bar engaged with or fixedly secured to the central portion of the actuation sled and includes a cutting edge positioned above the actuation sled. The retractor link is formed of a resilient material and has a proximal portion and a distal portion. The distal portion defines a longitudinal axis. The retractor link has a non-deformed condition and a deformed condition. In the non-deformed condition, the proximal portion of the retractor link bends outwardly from the longitudinal axis defined by the distal portion of the retractor link, and in the deformed condition, the proximal portion of the retractor link is substantially aligned with the longitudinal axis of the distal portion of the retractor link.

In aspects of the disclosure, the proximal portion of the retractor link includes an engaging member.

In some aspects of the disclosure, the engaging member includes a bend formed on the proximal portion of the retractor link.

In certain aspects of the disclosure, the engaging member includes a protrusion formed on the proximal portion of the retractor link.

In aspects of the disclosure, the recess is formed in the working member of the drive assembly.

In some aspects of the disclosure, the recess is formed in the flexible drive beam of the drive assembly.

In certain aspects of the disclosure, the retractor link is formed from spring steel.

In some aspects of the disclosure, the knife bar includes a base portion, and the central portion of the actuation sled is molded about the base portion of the knife bar to secure the knife bar to the actuation sled.

In certain aspects of the disclosure, the knife bar includes a body portion that defines a longitudinally extending recess and the distal portion of the retractor link is secured within the longitudinally extending recess.

Other aspects of the disclosure are directed to a surgical stapling device including a tool assembly and a drive assembly. The tool assembly includes an anvil and a cartridge assembly. The cartridge assembly includes a staple cartridge having a cartridge body, pushers, staples, and an actuation sled assembly. The cartridge body defines a knife slot and staple receiving pockets positioned on each side of the knife slot. Each of the staple receiving pockets receives one of the staples and one of the pushers. The actuation sled assembly includes an actuation sled, a knife bar, and a retraction link. The actuation sled includes a central portion and spaced wedge members positioned on opposite sides of the central portion. The central portion is received and movable within the knife slot. The knife bar includes a cutting edge that is positioned above the actuation sled and extends from the knife slot. The retractor link is formed of a resilient material and has a proximal portion and a distal portion. The distal portion of the retractor link defines a longitudinal axis. The retractor link has a non-deformed condition and a deformed condition. In the non-deformed condition, the proximal portion of the retractor link bends outwardly from the longitudinal axis of the distal portion of the retractor link and outwardly of the knife slot, and in the deformed condition, the proximal portion of the retractor link is substantially aligned with the longitudinal axis of the distal portion of the retractor link. The proximal portion of the retractor link includes an engaging member. The drive assembly includes a flexible drive beam and a working end that is secured to the flexible drive beam. The drive assembly is movable between retracted and advanced positions in relation to the tool assembly to eject the staples from the cartridge body. The drive assembly defines a recess that receives the engaging member of the retractor link when the retractor link is in the deformed condition to couple the knife bar of the actuation sled assembly to the drive assembly.

In aspects of the disclosure, the stapling device includes an adapter assembly having a proximal portion and a distal portion that supports the tool assembly.

In some aspects of the disclosure, the stapling device includes a handle assembly that is coupled to the proximal portion of the adapter assembly.

In certain aspects of the disclosure, the cartridge assembly is coupled to the anvil to facilitate movement of the tool assembly between unclamped and clamped positions.

In aspects of the disclosure, the drive assembly is movable from the retracted position to a drive assembly clamped position to move the tool assembly from the unclamped position to the clamped position.

In some aspects of the disclosure, the drive assembly is movable independently of the actuation sled assembly between the retracted position and the drive assembly clamped position.

Other features of the disclosure will be appreciated from the following description.

BRIEF DESCRIPTION OF THE DRAWINGS

Various aspects of the disclosed surgical stapling device are described herein below with reference to the drawings, wherein.

DETAILED DESCRIPTION

Figure 1:
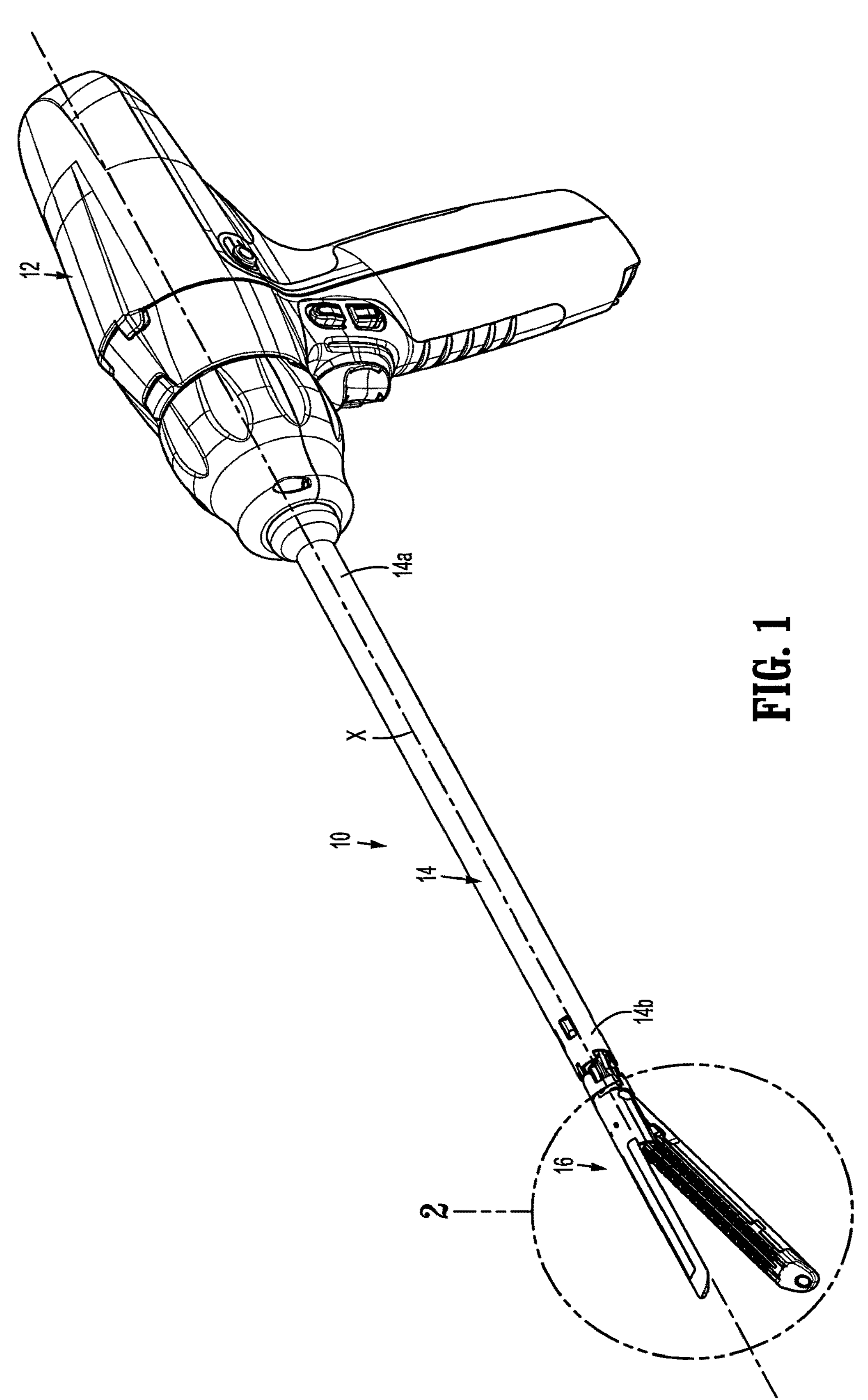
FIG. 1 is a side perspective view of a surgical stapling device according to aspects of the disclosure with a tool assembly of the stapling device in an open position.

The disclosed surgical stapling device will now be described in detail with reference to the drawings in which like reference numerals designate identical or corresponding elements in each of the several views. However, it is to be understood that disclosed aspects of the surgical stapling device are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

In this description, the term "proximal" is used generally to refer to that portion of the device that is closer to a clinician during use of the device in its customary fashion, while the term "distal" is used generally to refer to that portion of the device that is farther from the clinician during use of the device in its customary fashion. In addition, directional terms such as front, rear, upper, lower, top, bottom, and similar terms are used to assist in understanding the description and are not intended to limit the disclosure. Further, the term "clinician" is used generally to refer to medical personnel including doctors, nurses, surgeons, and support personnel.

The disclosure is directed to a surgical stapling device that includes a tool assembly having a drive assembly, an anvil, and a cartridge assembly. The cartridge assembly includes a replaceable staple cartridge that includes an actuation sled assembly having an actuation sled, a knife bar, and a retractor link. The retractor link is secured to the knife bar such that the actuation sled assembly is movable through a cartridge body of the staple cartridge. The retractor link is movable from a non-deformed condition disengaged from the drive assembly to a deformed condition engaged with the drive assembly to facilitate retraction of the actuation sled assembly after the stapling device is fired.

FIG. 1 illustrates a surgical stapling device shown generally as stapling device 10 that includes a handle assembly 12, an adapter assembly 14, and a tool assembly 16. The handle assembly 12 is powered and includes a stationary handgrip 18 and actuation buttons 20. The actuation buttons 20 are operable to actuate various functions of the tool assembly 16 via the adapter assembly 14, i.e., approximation of the tool assembly 16, and firing of the tool assembly 16. In certain aspects of the disclosure, the handle assembly 12 includes a motor (not shown) batteries (not shown), and circuitry that couples the batteries to the motor to operate the stapling device 10. Although the stapling device 10 is illustrated as a powered stapling device, it is envisioned that the advantages of this disclosure are suitable for use with manually powered surgical stapling devices as well as robotically controlled stapling devices. U.S. Pat. No. 5,865,361 describes a stapling device that includes exemplary aspects of a manually powered stapling device.

The adapter assembly 14 defines a longitudinal axis "X" and includes a proximal portion **14*a* and a distal portion 14*b*. The proximal portion 14*a* of the adapter assembly 14 is coupled to the handle assembly 12, and the distal portion 14*b* of the adapter assembly 14 is coupled to the tool assembly 16**.

Figures 2, 3:
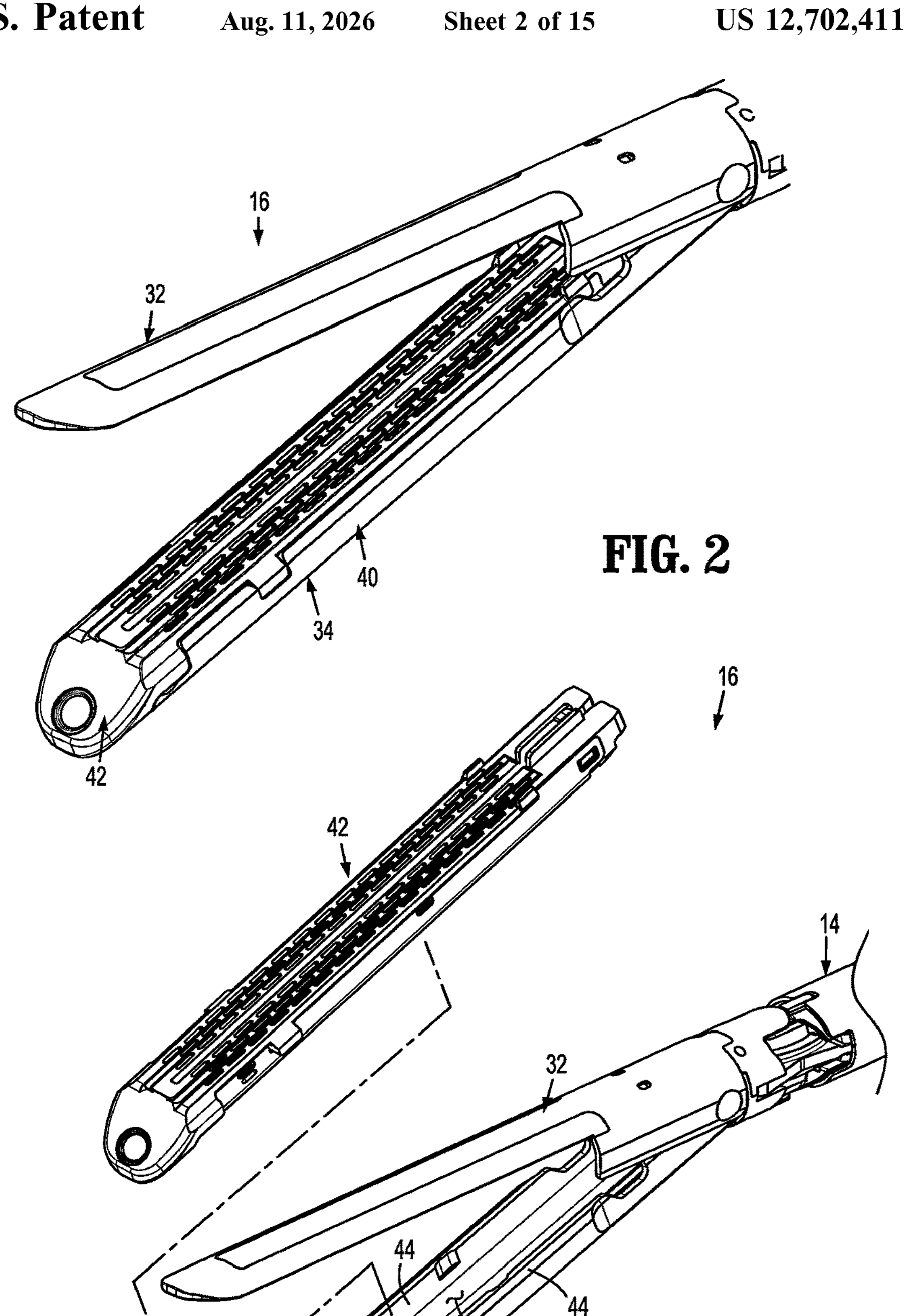
FIG. 2 is an enlarged view of the indicated area of detail of FIG. 1.
FIG. 3 is a side perspective view of the tool assembly of the stapling device shown in FIG. 1 with a staple cartridge of a cartridge assembly of the tool assembly separated from a channel of the cartridge assembly.
Figures 11, 12:
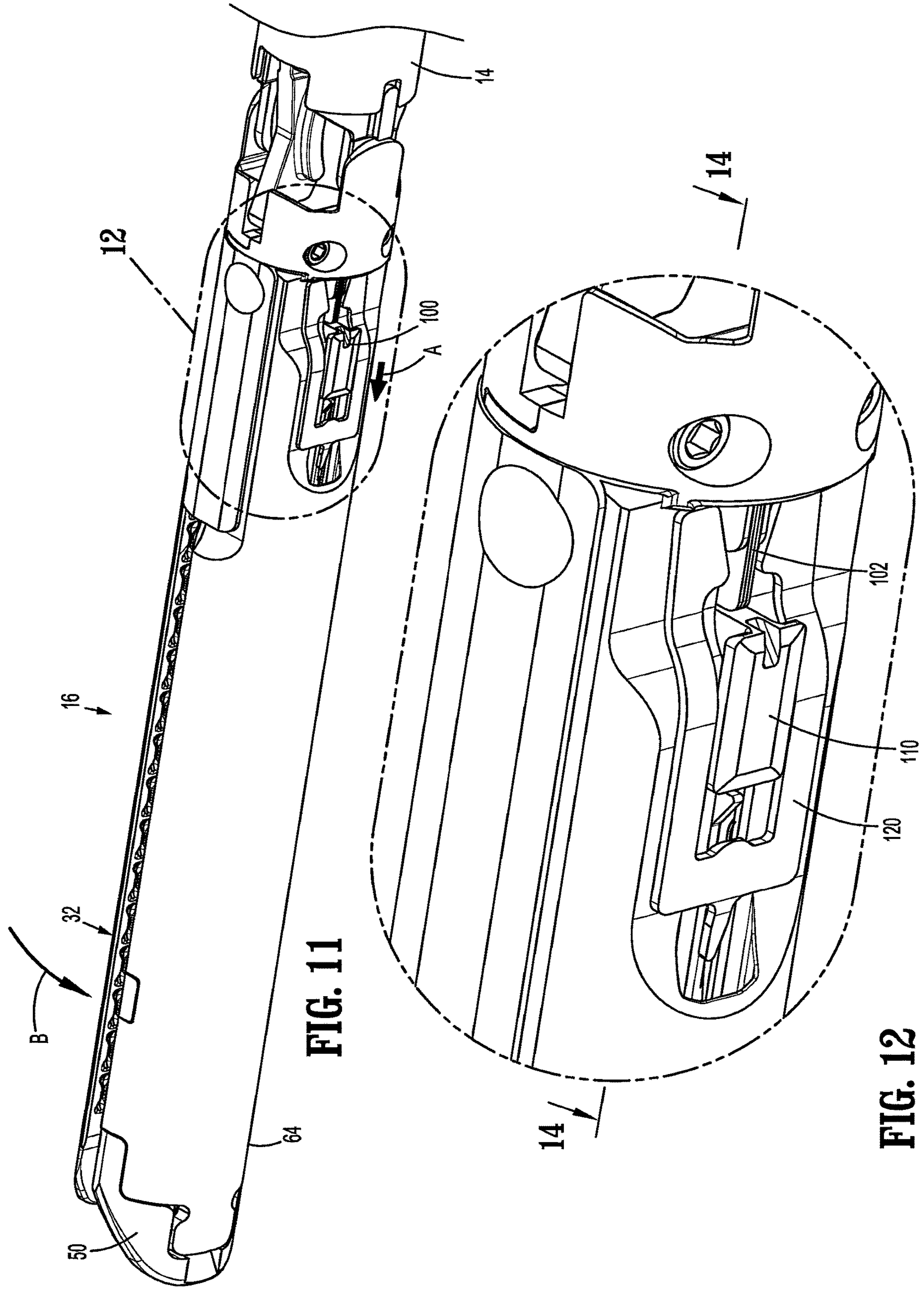
FIG. 11 is a side view of the tool assembly shown in FIG. 2 with the tool assembly moved to the clamped position and the channel member removed.
FIG. 12 is an enlarged view of the indicated area of detail shown in FIG. 11.

FIGS. 2 and 3 illustrate the tool assembly 16 which includes an anvil 32 and a cartridge assembly 34. In aspects of the disclosure, the cartridge assembly 34 is pivotably supported in relation to the anvil 32 and the adapter assembly 14 such that the tool assembly 16 is movable between an open position (FIG. 2) and a clamped position (FIG. 11). Alternately, it is envisioned that the anvil 32 may be pivotably supported in relation to the cartridge assembly 34 and the adapter assembly 14.

FIGS. 2-5 illustrate the cartridge assembly 34 which includes a channel member 40 and a staple cartridge 42. The channel member 40 includes side walls 44 and a bottom wall 46 that define a cavity 48. The staple cartridge 42 is removably received within the cavity 48 of the channel member 38 and is replaceable to facilitate reuse of the stapling device 10. Each of the side walls 44 defines a recess 49 (FIG. 3) on an upper edge of the side wall 44.

Figures 4, 5:
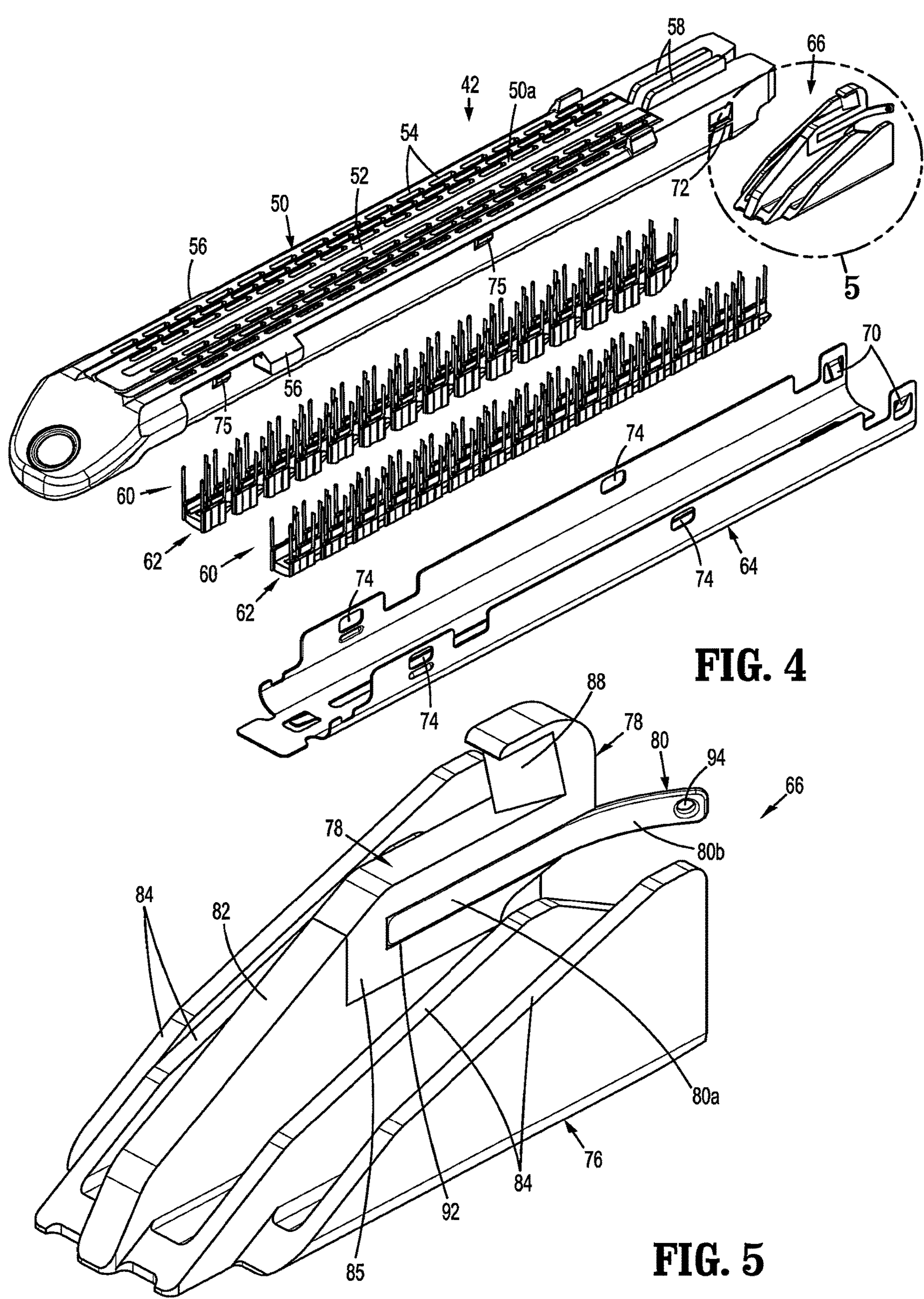
FIG. 4 is a side perspective exploded view of the staple cartridge of the cartridge assembly of the tool assembly shown in FIG. 3.
FIG. 5 is an enlarged view of the indicated area of detail shown in FIG. 4 illustrating an actuation sled assembly of the staple cartridge shown in FIG. 4.

FIG. 4 illustrates the staple cartridge 42 which includes a cartridge body 50 that defines a knife slot 52 and staple receiving pockets 54 positioned on each side of the knife slot 52. In aspects of the disclosure, the knife slot is centrally located along a longitudinal axis of the cartridge body 50. In aspects of the disclosure, the staple receiving pockets 54 are aligned in two or more rows on opposite sides of the knife slot 52. The cartridge body 50 includes laterally extending protrusions 56 that are received within the recesses 49 (FIG. 3) of the channel member 40 (FIG. 3) to properly position the staple cartridge 40 within the cavity 46 of the channel member 38. The cartridge body 50 also includes knife guards 58 that are positioned on opposite sides of the knife slot 52 at a proximal portion of the cartridge body 50.

The staple cartridge 42 includes staples 60, pushers 62, a staple guard 64, and an actuation sled assembly 66. The staples 60 are supported on the pushers 62 and received within the staple receiving pockets 54 of the cartridge body 50. The staple guard 64 is U-shaped and is secured to the bottom of the cartridge body 50 to retain the staples 60 and pushers 62 within the cartridge body 50. In aspects of the disclosure, the staple guard 64 includes resilient fingers 70 that are received in snap-fit fashion in recesses 72 in the cartridge body 50 to secure a proximal portion of the staple guard 64 to the cartridge body 50. The staple guard 64 may also include openings 74 that receive protrusions 75 on the cartridge body 50 to retain the staple guard 64 on the cartridge body 50.

FIGS. 5-12 illustrate the actuation sled assembly 66 which includes an actuation sled 76, a knife bar 78, and a retractor link 80. The actuation sled assembly 66 is received in the cartridge body 50 of the staple cartridge 42 and is movable within the cartridge body 50 between sled retracted and sled advanced positions. The actuation sled 76 includes a central portion 82 and spaced wedge members 84 that are positioned on opposite sides of the central portion 82. The wedge members 84 are configured to engage and lift the pushers 62 as the actuation sled assembly 66 is moved from the sled retracted position to the sled advanced position to eject the staples 60 from staple receiving pockets 54 of the cartridge body 50. The central portion 82 of the actuation sled 76 is received in the knife slot 52 of the cartridge body 50 and is movable through the knife slot 52 to limit the actuation sled assembly 66 to linear movement.

The knife bar 78 is fixedly secured to the central portion 82 of the actuation sled 76 and includes a body portion 85, a base portion 86, and knife 88. The body portion 85 of the knife bar 78 is received in and movable through the knife slot 52. The knife 88 is supported on an upper surface of the body portion 85 and includes a distally facing cutting edge **88*a*. The cutting edge 88*a* extends upwardly from the body portion 85 to a position above a tissue engaging surface 50*a* of the cartridge body 50 and is shielded by the knife guards 58 (FIG. 4). The knife guards 58 may be integrally formed with the cartridge body 50 or secured thereto. The base portion 86 extends downwardly from the body portion 85 and is secured to the central portion 82 of the actuation sled 76. In aspects of the disclosure, the base portion 86 defines two openings 90 that receive portions of the central portion 82 of the actuation sled 76. In certain aspects of the disclosure, the actuation sled 76 is formed of plastic and the knife bar 78 is formed from metal, and the actuation sled 76 is molded about the base portion 86 of the knife bar 78**.

Figures 6A, 6B, 7:
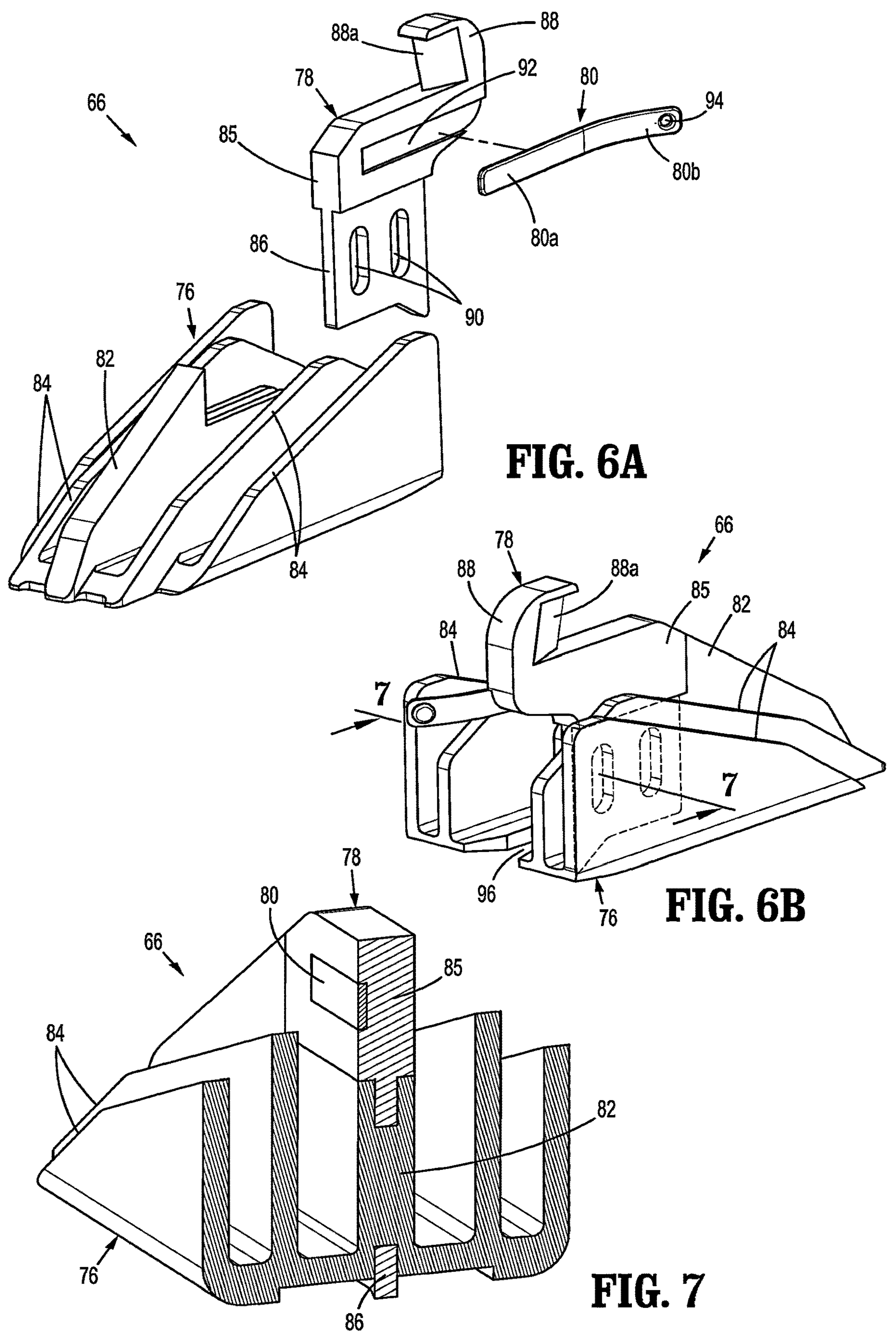
FIG. 6A is a side perspective, exploded view of the actuation sled assembly shown in FIG. 5.
FIG. 6B is a perspective view from a proximal end of the actuation sled assembly shown in FIG. 5.
FIG. 7 is a cross-sectional view taken along section line 7-7 of FIG. 6B.
Figures 8, 9, 10:
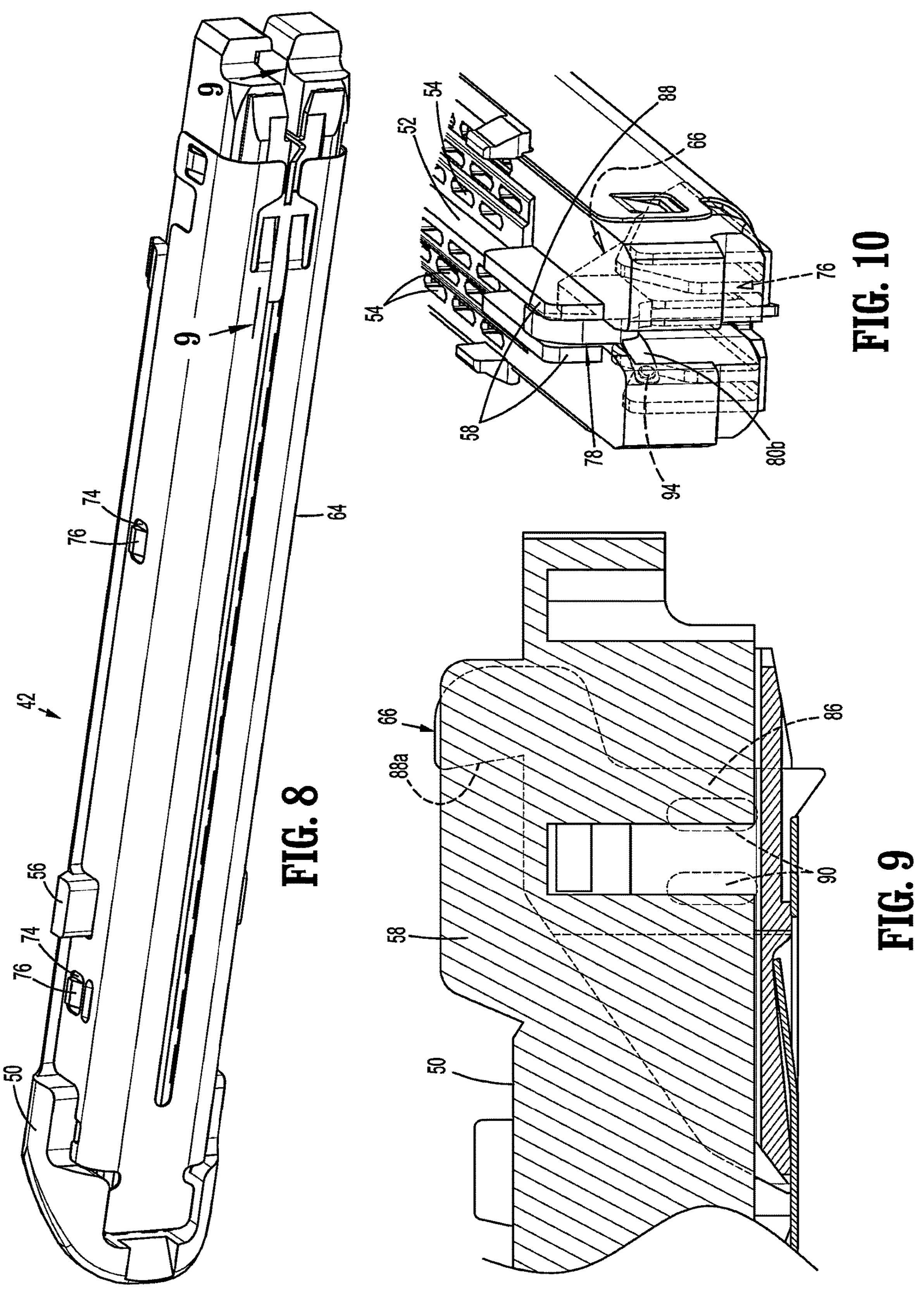
FIG. 8 is a bottom, perspective view of the staple cartridge of the cartridge assembly shown in FIG. 4.
FIG. 9 is a cross-sectional view taken along section line 9-9 of FIG. 8.
FIG. 10 is a perspective view of a proximal portion of the staple cartridge shown in FIG. 8 with the actuation sled assembly shown in FIG. 8.

The retractor link 80 is secured to the body portion 85 of the knife bar 78 in cantilevered fashion. In aspects of the disclosure, the retractor link 80 is formed of a resilient material, e.g., spring steel, and includes a distal portion **80*a* and a proximal portion 80*b*. The proximal portion 80*b* of the retractor link 80 includes an engaging member which may be in the form of an inwardly extending protrusion 94. The distal portion 80***a* defines a longitudinal axis and is secured to the central portion 82 of the knife bar 78, and the proximal portion 80*b* extends proximally from the actuation sled 76. In aspects of the disclosure, the body portion 85 of the knife bar 78 defines a longitudinally extending recess 92 (FIG. 6A), and the distal portion 80*a* of the retractor link 80 is secured within the recess 92. The retractor link 80 is movable between a non-deformed condition and a deformed condition. In the non-deformed condition, the proximal portion of the retractor link 80 bends outwardly from the longitudinal axis defined by the distal portion 80 of the retractor link 80 and outwardly of the knife slot 52 of the cartridge body 50. When the actuation sled assembly 66 is advanced through the knife slot 52, the proximal portion 80*b* of the retractor link 80 engages an inner wall of the cartridge body 50 defining the knife slot 52 and is moved to the deformed condition in which the distal and proximal portions 80*a*, 80*b* of the retractor link 80 are longitudinally aligned. The actuation sled 76 of the actuation sled assembly 66 includes a proximal portion that defines a centrally located cutout 96 (FIG. 6B).

Figure 13:
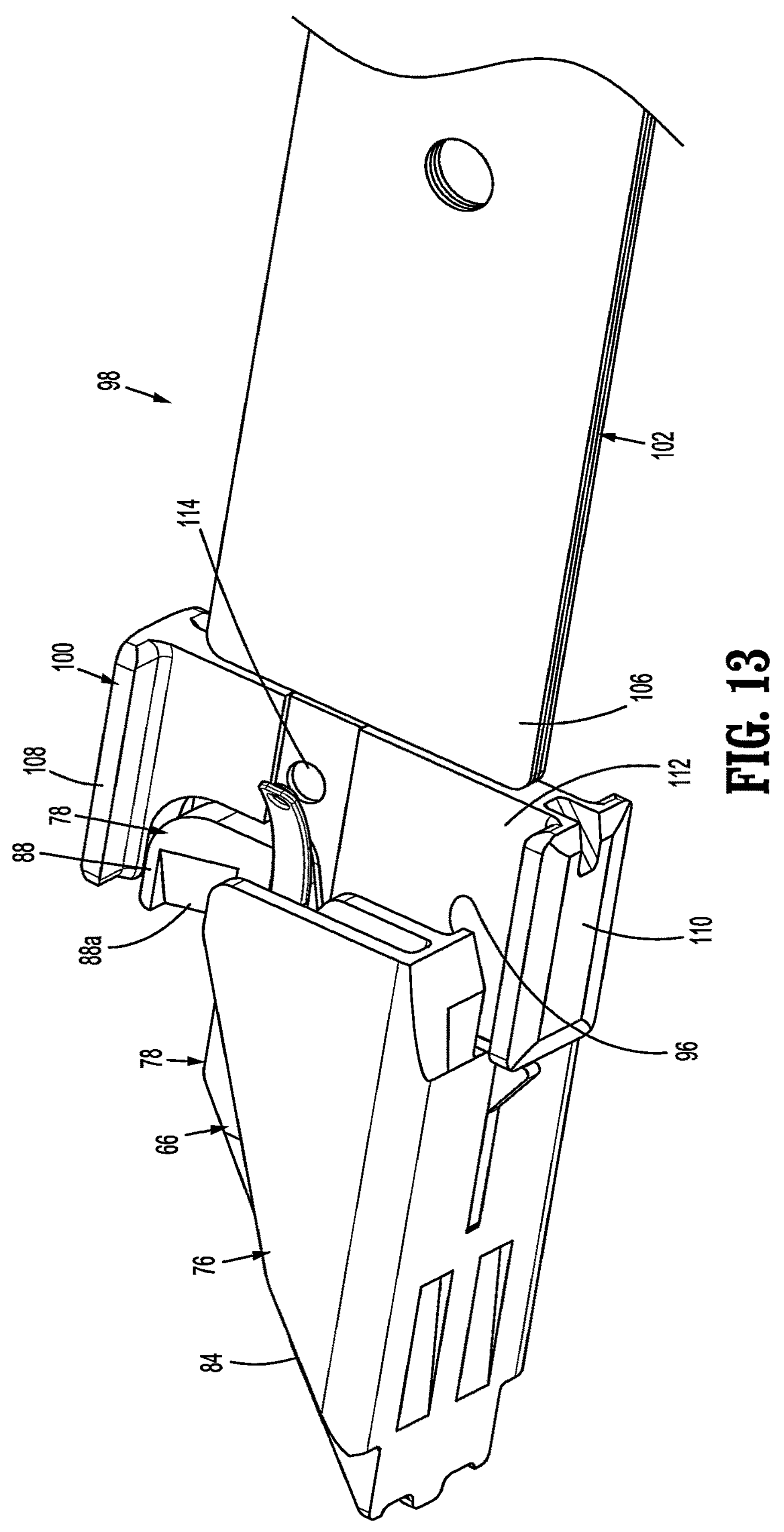
FIG. 13 is a side perspective view of a drive assembly and the actuation sled assembly of the surgical stapling device shown in FIG. 1 in retracted positions.

The stapling device 10 includes a drive assembly 98 illustrated in FIG. 13 which includes a working member 100 and a flexible drive beam 102. The working member 100 of the drive assembly 98 is partly received in the cutout 96 of the actuation sled 76 when the drive assembly 98 is in a clamped position and the actuation sled assembly 66 is in a retracted position. The drive assembly 98 is movable from a retracted position, through a drive assembly clamped position, to advanced position and includes a flexible drive beam 102 that has a proximal portion (not shown) and a distal portion 106 that is secured to the working member 100. In aspects of the disclosure, the flexible drive beam 102 is formed from stacked laminates. Alternately, other configurations of the flexible drive beam 102 are envisioned. When the drive assembly 98 is moved from the retracted position to the drive assembly clamped position, the working member 100 moves independently of the actuation sled assembly 66 to move the tool assembly 16 (FIG. 1) from the unclamped position to the clamped position.

The working member 100 of the drive assembly 98 has an I-shaped configuration and includes a first beam 108, a second beam 110, and a vertical strut 112 that connects the first beam 108 to the second beam 110. The vertical strut 112 is aligned with the knife slot 52 (FIG. 16) in the cartridge body 50 and is positioned to engage the actuation sled assembly 66. When the drive assembly 98 moves from the retracted position to the clamped position in the direction of arrow “A” in FIG. 11, the first and second beams 108, 110 engage the anvil 32 and the cartridge assembly 34 to pivot the cartridge assembly 34 in the direction of arrow “B” in FIG. 11. In the clamped position of the drive assembly 98, the working member 100 of the drive assembly 98 is received in the cutout 96 of the actuation sled 76 of the actuation sled assembly 66 and is in close approximation or abutting relation to the actuation sled assembly 66. When the drive assembly 98 is moved from the clamped position towards the advanced position, the vertical strut 112 of the working member 100 of the drive assembly 98 engages and advances the actuation sled assembly 66 through the knife slot 52 to move the actuation sled assembly 66 between the sled retracted and advanced positions.

The vertical strut 112 of the working member 100 of the drive assembly 98 defines a recess or opening 114. When the actuation sled assembly 66 is moved by the drive assembly 98 from the sled retracted position towards the sled advanced position, the retractor link 80 of the actuation sled assembly 66 moves with the actuation sled assembly 66 into the knife slot 52 of the cartridge body 50. As the proximal portion 80*b* of the retractor link 80 moves into the knife slot 52 of the cartridge body 50, engagement of the proximal portion 80*b* of the retractor link 80 with the cartridge body 50 moves the retractor link 80 from the undeformed condition to the deformed condition. When this occurs, the protrusion 94 of the retractor link 80 is received in the recess or opening 114 formed in the vertical strut 112 to secure the actuation sled assembly 66 to the working member 100 of the drive assembly 98.

Figure 14:
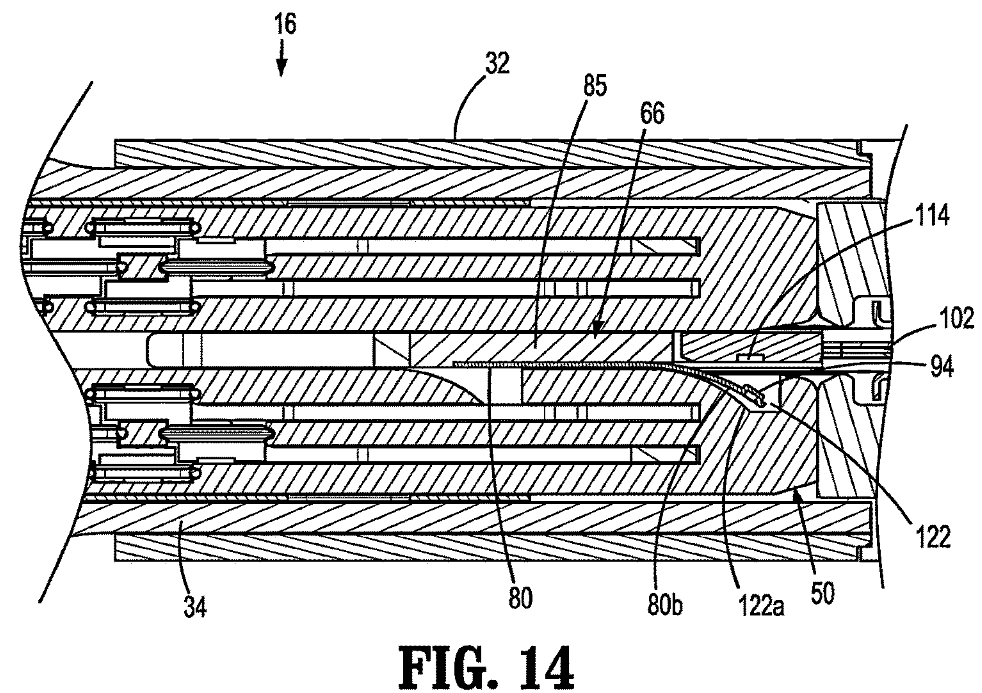
FIG. 14 is a cross-sectional view taken along section line 14-14 of FIG. 12.
Figure 15:
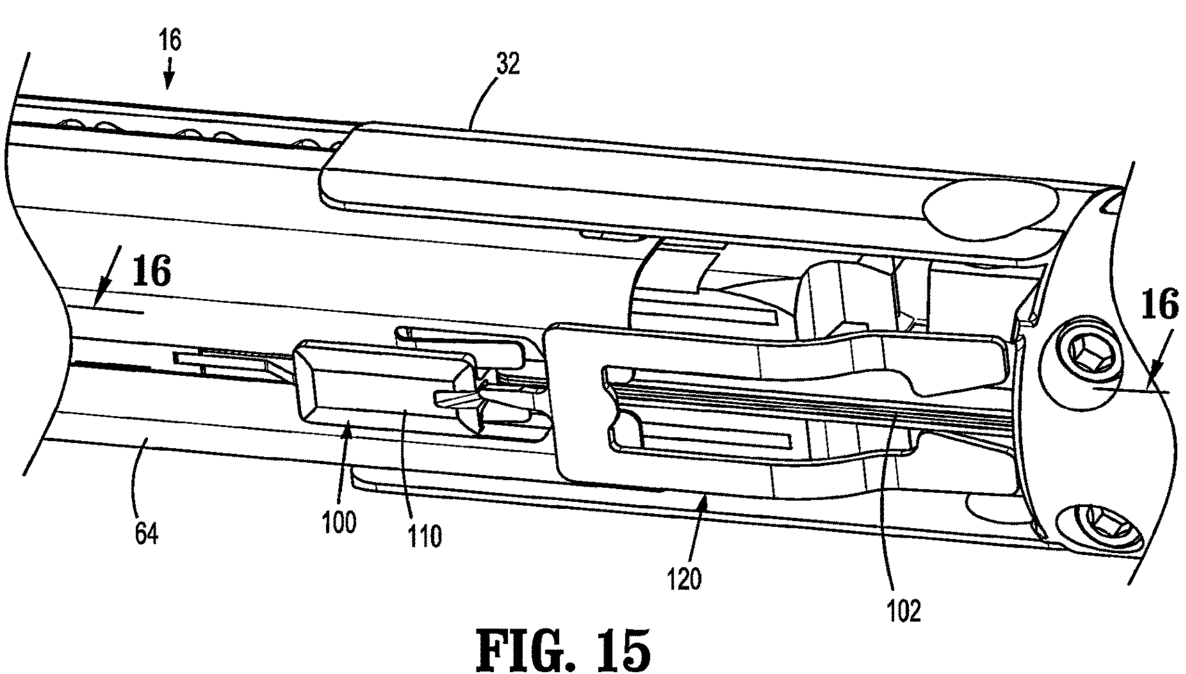
FIG. 15 is a side cutaway view of a proximal portion of the tool assembly with the channel of the cartridge assembly removed as the tool assembly is fired.

FIGS. 13-15 illustrate the tool assembly 16 with the drive assembly 98 in the drive assembly clamped position and the actuation sled assembly 66 in the sled retracted position. Although not described in detail herein, the cartridge assembly 34 includes a lockout member 120 that prevents refiring of the tool assembly 16 with a spent staple cartridge. The lockout member 120 does not form part of this disclosure and will not be described in further detail herein. When the drive assembly 98 is in the clamped position, and the actuation sled assembly 66 is in the sled retracted position, the retractor link 80 is in its non-deformed condition in which the proximal portion 80*b* of the retractor link 80 is bent outwardly of the knife slot 52 of the cartridge body 50. To accommodate the proximal portion 80*b* of the retractor link 80 when the retractor link 80 is in the non-deformed condition, the cartridge body 50 defines a pocket 122 (FIG. 14) that includes a curved wall 122*a* that has a curvature that corresponds to the curvature of the proximal portion 80*b* of the retractor link 80 in the non-deformed condition.

Figure 16:
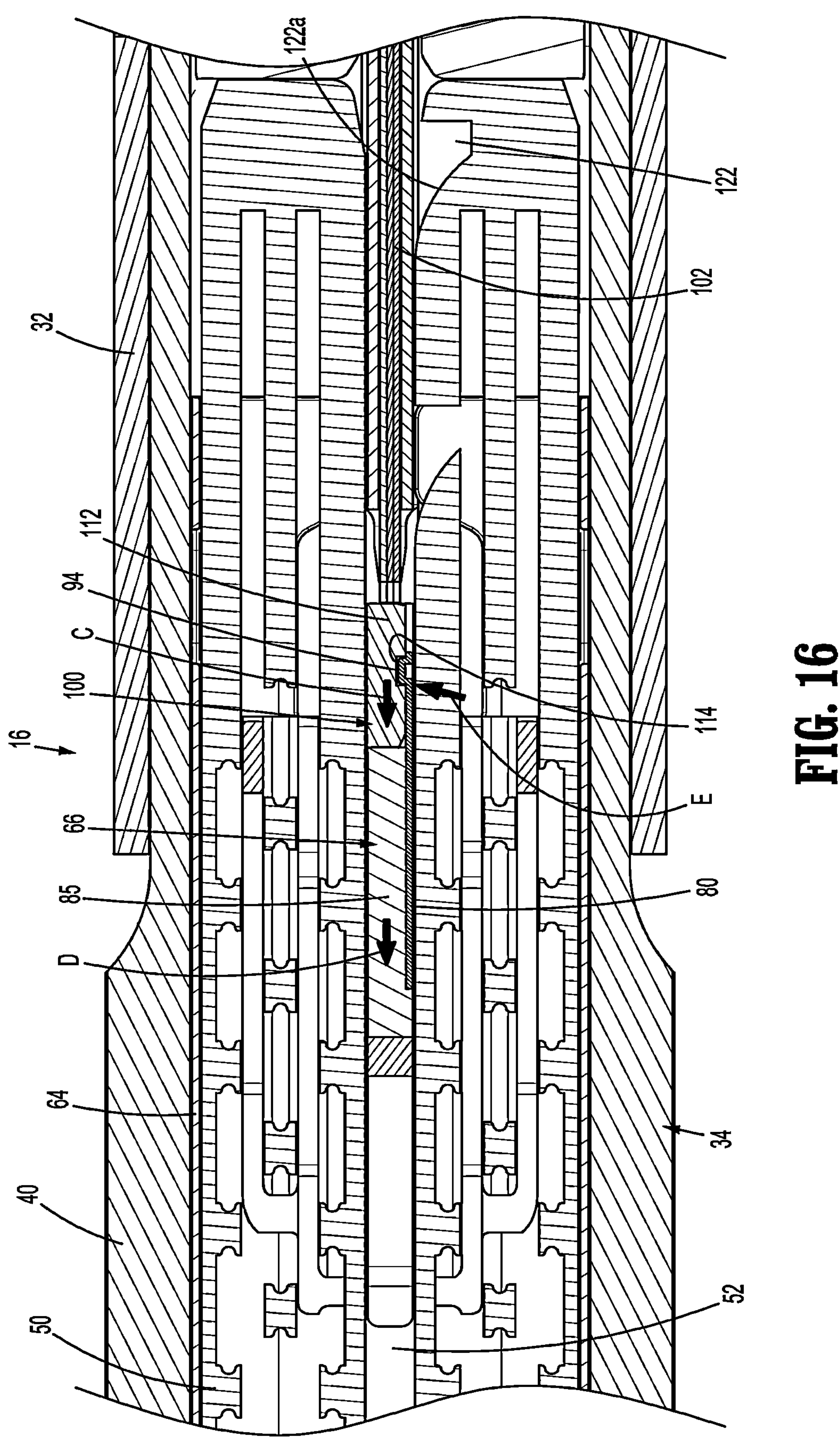
FIG. 16 is a cross-sectional view taken along section line 16-16 of FIG. 15.

FIG. 16 illustrates the tool assembly 16 as the drive assembly 98 is moved from the clamped position towards the advanced position to move the actuation sled assembly 66 from the sled retracted position (FIG. 14) towards the sled advanced position. When the drive assembly moves in the direction of arrow “C” from the drive assembly clamped position towards the advanced position, the working member 100 of the drive assembly 98 moves the actuation sled assembly 66 in the direction of arrow “D”. As the proximal portion 80*b* of the retractor link 80 moves into the knife slot 52 of the cartridge body 50, the proximal portion 80*b* of the retractor link 80 engages the curved wall 122*a* of the cartridge body 50 and is moved from the undeformed condition to the deformed condition in the direction of arrow “E”. As the retractor link 80 moves to the deformed condition, the protrusion 94 of the retractor link 80 is received within the recess 114 formed in the vertical strut 112 of the working member 100 to couple the actuation sled assembly 66 to the working member 100 of the drive assembly 98. As the drive member 98 moves towards the advanced position to move the actuation sled assembly 66 towards the sled advanced position, the spaced wedge members 84 (FIG. 13) of the actuation sled 76 engage the pushers 62 (FIG. 4) of the staple cartridge 42 to eject the staples 60 from the staple receiving slots 54 of the cartridge body 50 into the anvil 32.

Figure 17:
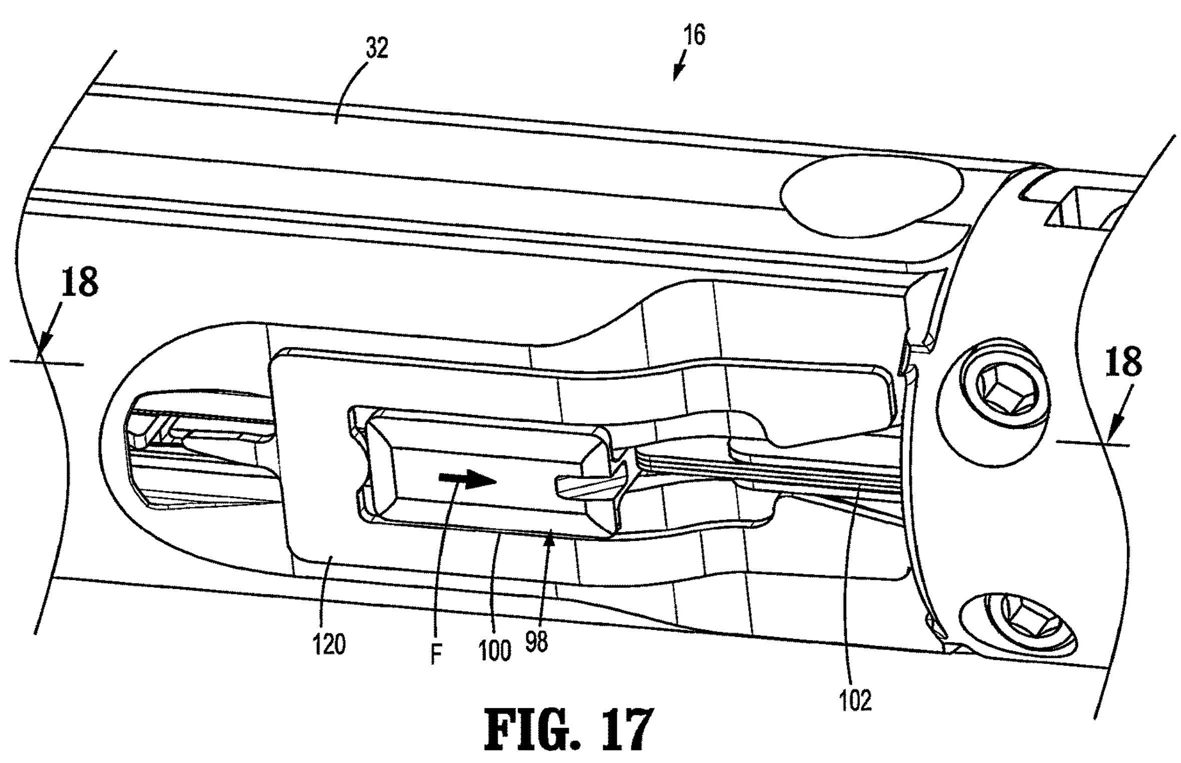
FIG. 17 is a side cutaway view of the proximal portion of the tool assembly with the channel of the cartridge assembly removed as the drive assembly is returned to its retracted position after the stapling device has been fired.
Figure 18:
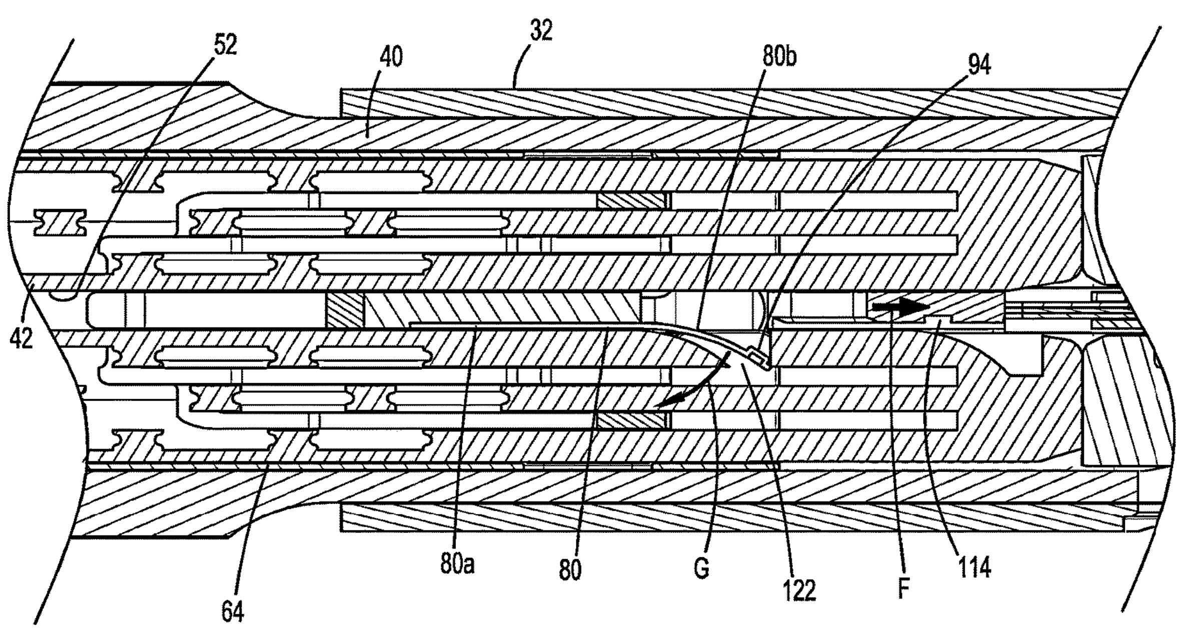
FIG. 18 is a cross-sectional view taken along section line 18-18 of FIG. 17.
Figure 19:
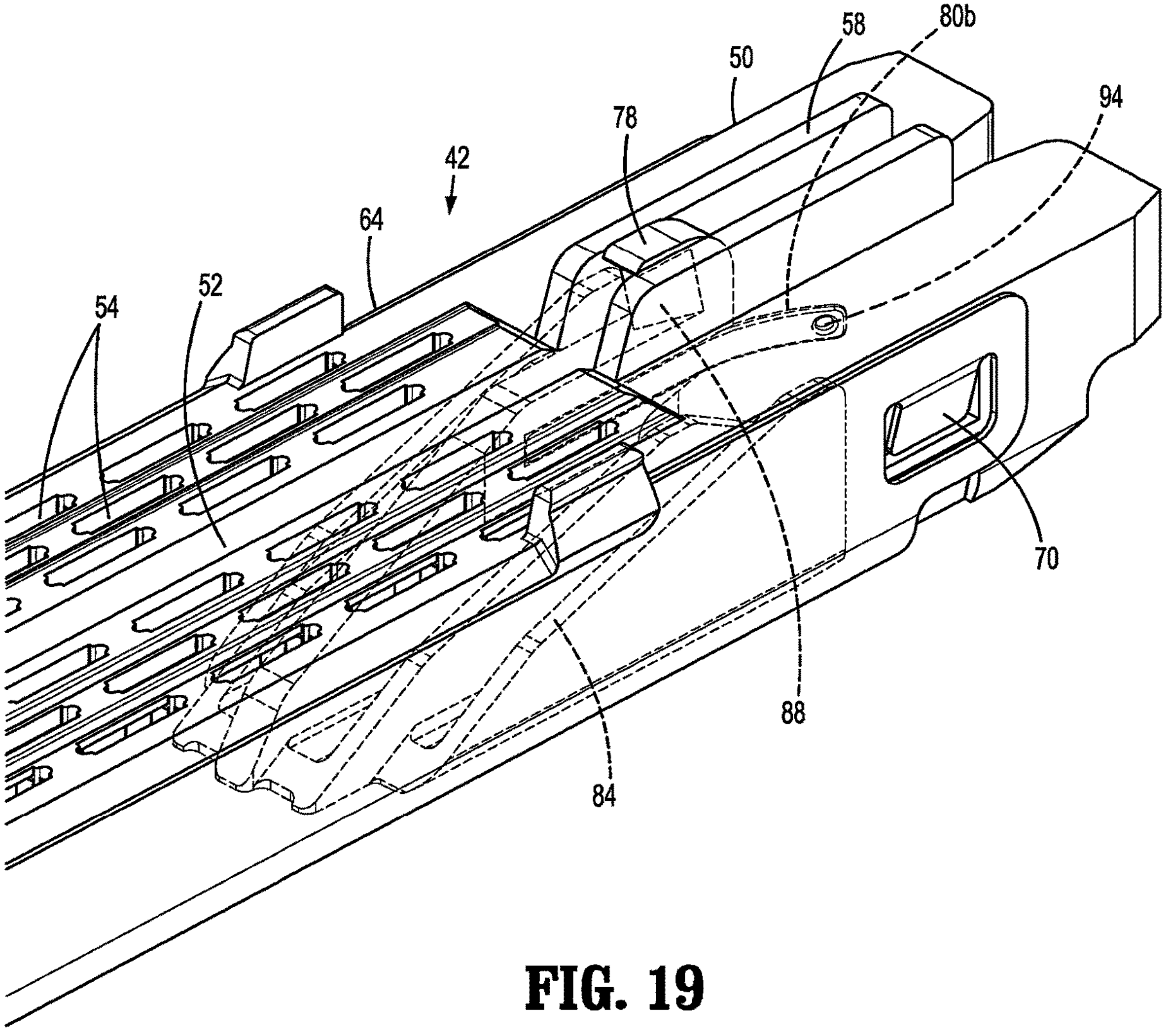
FIG. 19 is a side perspective view from above of the proximal portion of the staple cartridge after the staple cartridge has been fired and removed from the channel of the cartridge assembly.

FIGS. 17 and 18 illustrate the tool assembly 16 as the drive assembly 98 is returned from the advanced position to the retracted position in the direction of arrow “F”. As described above, the protrusion 94 of the retractor link 80 is received in the recess or opening 114 in the vertical strut 112 of the working member 100 of the drive assembly 98 to couple the actuation sled assembly 66 to the drive assembly 98. Thus, as the drive assembly 98 returns from the advanced position to the retracted position, the actuation sled assembly 66 also moves from the sled advanced position to the sled retracted position. When the actuation sled assembly 66 returns to the sled retracted position and the drive assembly 98 is returned to the drive assembly clamped position, the proximal portion 80*b* of the retractor link 80 becomes aligned with the pocket 122 in the cartridge body 50. When this occurs, the proximal portion 80*b* of the retractor link 80 returns to the non-deformed position in the direction of arrow "G" in FIG. 18 to uncouple the actuation sled assembly 66 from the drive assembly 98. After the actuation sled assembly 66 is uncoupled from the drive assembly 98, the drive assembly 98 continues to move towards the retracted position independently of the actuation sled assembly 66. In this position, the spent staple cartridge 42 (FIG. 19) can be removed from channel member 34 (FIG. 3) and replaced with a fresh staple cartridge to facilitate reuse of the stapling device 10 (FIG. 1).

Figures 20, 21, 22:
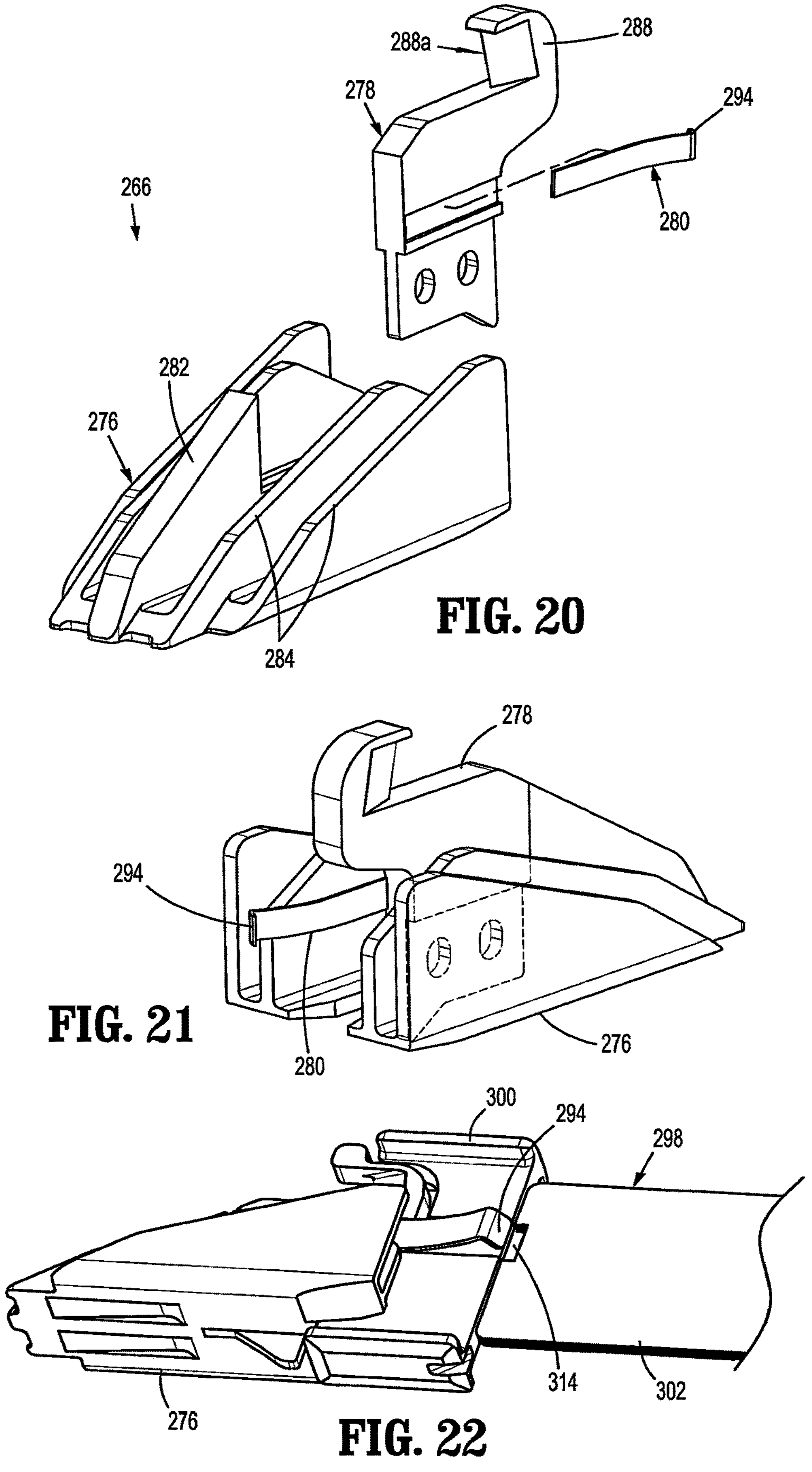
FIG. 20 is a side perspective view of an alternate version of the actuation sled assembly of the surgical stapling device shown in FIG. 1.
FIG. 21 is a side perspective, exploded view of a knife assembly of the actuation sled assembly shown in FIG. 20.
FIG. 22 is a side perspective view of an alternate version of the drive assembly of the surgical stapling device shown in FIG. 1 in their retracted positions.
Figures 23, 24:
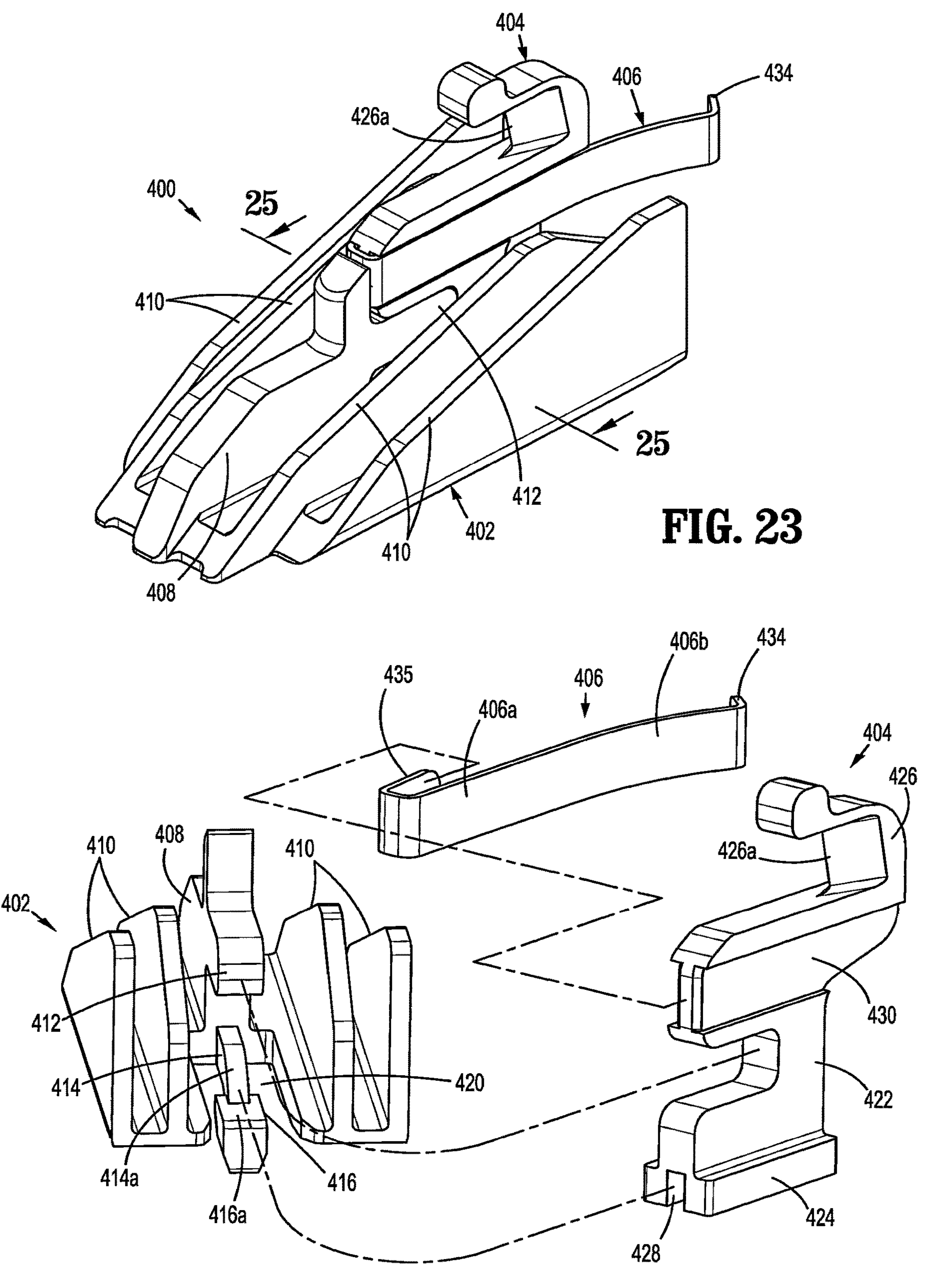
FIG. 23 is a side perspective view of an alternate version of the actuation sled assembly of the surgical stapling device shown in FIG. 1.
FIG. 24 is an exploded view of the actuation sled assembly of FIG. 23.
Figure 25:
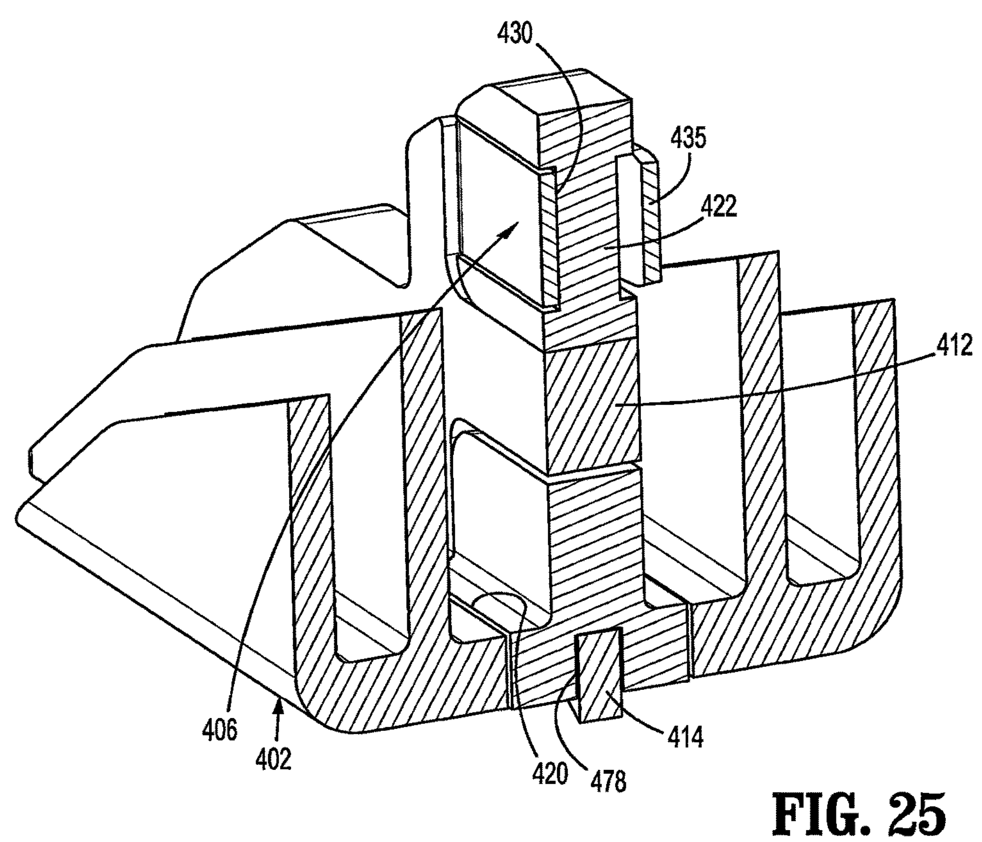
FIG. 25 is a cross-sectional view taken along section line 25-25 of FIG. 23.
Figure 26:
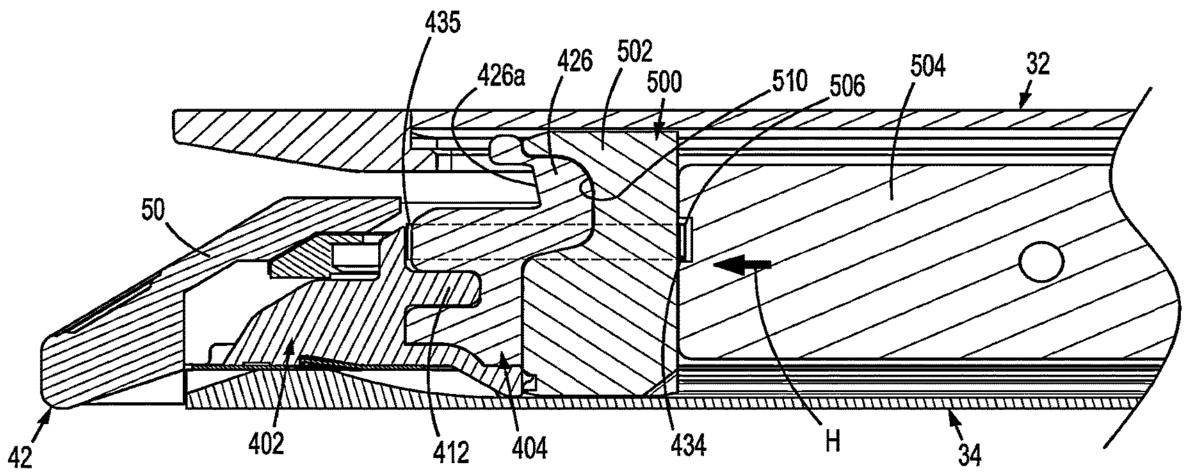
FIG. 26 is a cross-sectional view taken through the distal portion of the tool assembly with the stapling device in the clamped and fired position and the drive assembly in the advanced position.

FIGS. 20-22 illustrate an alternate version of the actuation sled assembly shown generally as actuation sled assembly 266 and the drive assembly shown generally as drive assembly 298 (FIG. 22). The actuation sled assembly 266 is like actuation sled assembly 66 (FIG. 6A) and includes an actuation sled 276, a knife bar 278, and a retractor link 280. The knife bar 278 includes a knife 288 having a distally facing cutting edge 288*a*. The actuation sled assembly 266 is received in the cartridge body 50 (FIG. 4) of the staple cartridge 42 and is movable within the cartridge body 50 between sled retracted and sled advanced positions. The actuation sled 276 includes a central portion 282, and spaced wedge members 284 that are positioned on opposite sides of the central portion 282. The wedge members 284 are configured to engage and lift the pushers 62 (FIG. 4) as the actuation sled assembly 266 is moved from the sled retracted position to the sled advanced position to eject the staples 60 (FIG. 4) from staple receiving pockets 54 of the cartridge body 50. The central portion 282 of the actuation sled 276 is received in the knife slot 52 (FIG. 4) of the cartridge body 50 and is movable through the knife slot 52 to limit the actuation sled assembly 266 to linear movement. The actuation sled assembly 266 differs from the actuation sled assembly 66 (FIG. 6A) in that the retractor link 280 includes a proximal portion that includes an engaging member in the form of a bend 294.

The drive assembly 298 is like the drive assembly 98 and includes a working member 300 and a flexible drive beam 302. The working member 300 and the flexible drive beam 302 are as described above regarding working member 100 and flexible drive beam 102 except that a distal portion of the flexible drive beam 302 defines a recess or opening 314. In some aspects of the disclosure, the recess or opening 314 may also be formed in the vertical strut 312 of the working member 300.

The actuation sled assembly 266 and the drive assembly 298 function in the same manner as the actuation sled assembly 66 and the drive assembly 98. More specifically, when the drive assembly 298 moves from the drive assembly clamped position towards the advanced position to move the actuation sled assembly 266 from the sled retracted position towards the sled advanced position, the retractor link 280 moves into the knife slot 52 (FIG. 4) and is deformed from the undeformed condition to the deformed condition. When this occurs, the bend 294 is received in the opening 314 defined in the drive assembly 298 to couple the actuation sled assembly 266 to the drive assembly 298.

Figure 27:
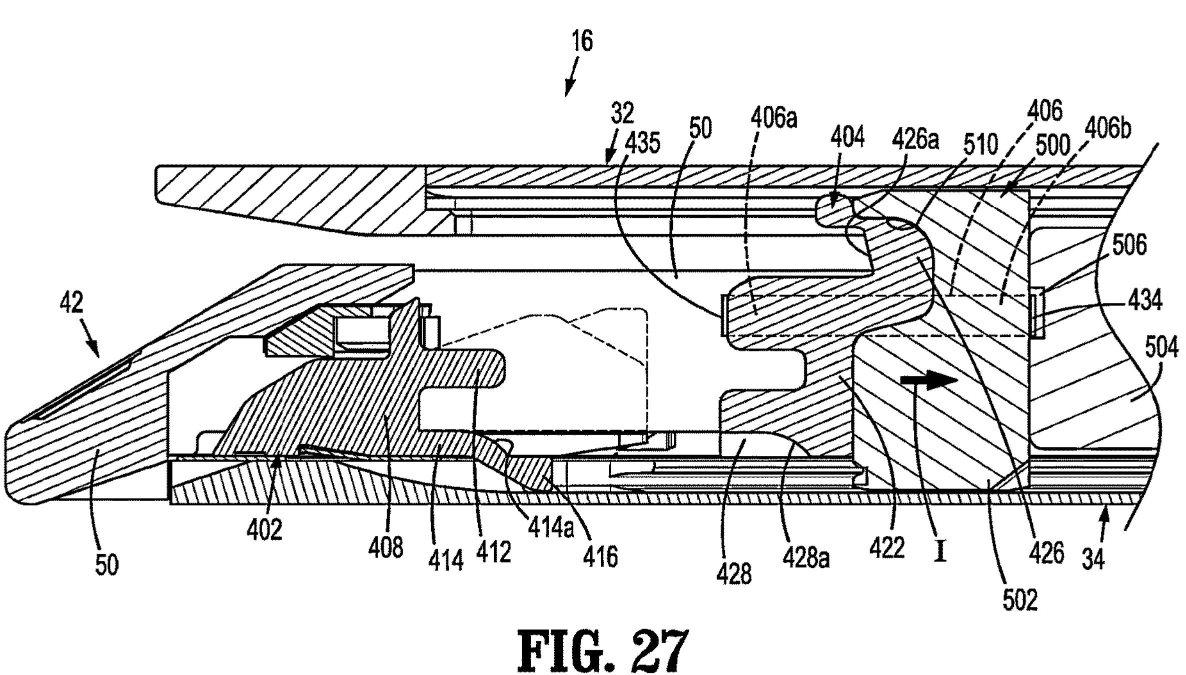
FIG. 27 is a cross-sectional view taken through the distal portion of the tool assembly with the stapling device in the clamped and fired position as the drive assembly moves from the advanced position back towards the retracted position with the knife bar coupled to the drive assembly.

FIGS. 23 to 28 illustrate an alternate version of the actuation sled assembly and drive assembly of the stapling device 10 (FIG. 1) shown as actuation sled assembly 400 and drive assembly 500 (FIG. 27). The actuation sled assembly 400 includes an actuation sled 402, a knife bar 404, and a retractor link 406. The actuation sled assembly 400 is like the actuation sled assemblies 66 (FIG. 5) and 266 (FIG. 21) except that the knife bar 404 is not secured to the actuation sled 402. The actuation sled assembly 400 is received in the cartridge body 50 (FIG. 27) of the staple cartridge 42 (FIG. 4) and is movable within the cartridge body 50 between sled retracted and sled advanced positions. The actuation sled 402 includes a central portion 408 and spaced wedge members 410 that are positioned on opposite sides of the central portion 408. The wedge members 410 are configured to engage and lift the pushers 62 (FIG. 4) as the actuation sled assembly 400 is moved from the sled retracted position towards the sled advanced position to eject the staples 60 (FIG. 4) from staple receiving pockets 54 (FIG. 4) of the cartridge body 50. The central portion 408 of the actuation sled 402 is received in the knife slot 52 of the cartridge body 50 and is movable through the knife slot 52 to limit the actuation sled assembly 400 to linear movement. The central portion 408 of the actuation sled 402 defines a proximally extending finger 412, a longitudinally extending rib 414 (FIG. 24), and a member 416 that has a flat surface 416*a*. The rib 414 has a curved proximal surface 414*a*. The actuation sled 402 also defines a cutout 420 between the wedge members 410 that is dimensioned to receive the knife bar 404 as described below. The rib 414 and the member 416 are received in the cutout 420 and the flat surface 416*a* of the member 416 extends proximally of the cutout 420.

The knife bar 404 includes a body portion 422, a base portion 424, and knife 426. The body portion 422 of the knife bar 404 is received in and movable through the knife slot 52 of the cartridge body 50 (FIG. 4). The knife 426 includes a distally facing cutting edge 426*a* and is supported on an upper end of the body portion 422 of the knife bar 404 and projects proximally of a lower portion of the body portion 422 of the knife bar 404. The cutting edge 426*a* extends upwardly from the body portion 422 of the knife bar 404 to a position above the tissue engaging surface 50*a* (FIG. 4) of the cartridge body 50 and is shielded by the knife guards 58 (FIG. 4) when the knife bar 404 is in the retracted position. The base portion 424 is secured to or formed on the lower end of the body portion 422 and defines a channel 428 (FIG. 24) that is positioned to receive the rib 414 of the actuation sled 402. The base portion 424 extends outwardly of the body portion 422 and is positioned to ride along a bottom wall of the staple guard 64 (FIG. 4). The channel 428 in the base portion 424 of the knife bar 404 is defined in part by a curved proximal portion 428*a* (FIG. 27) that is configured to engage the curved proximal surface 414*a* of the rib 414 when the knife bar 404 is engaged with the actuation sled 402. The body portion 422 of the knife bar 404 defines a longitudinally extending recess 430 (FIG. 24) that receives a distal portion 406*a* of the retractor link 406. In aspects of the disclosure, the actuation sled 402 is formed of plastic and the knife bar 404 is formed from metal.

The retractor link 406 is secured to the body portion 422 of the knife bar 404 in cantilevered fashion. In aspects of the disclosure, the retractor link 406 is formed of a resilient material, e.g., spring steel, and includes the distal portion 406*a* and a proximal portion 406*b*. The proximal portion 406*b* of the retractor link 406 includes an engaging member which may be in the form of a 90-degree bend 434. The distal portion 406*a* defines a longitudinal axis and is secured to the central portion 408 of the knife bar 404 within the recess 430. In aspects of the disclosure, the distal portion 406*a* of the retractor link 406 has a u-shaped portion 435 that receives the body portion 422 of the knife bar 404. The proximal portion 406*b* of the retractor link 406 extends proximally from the knife bar 404. The retractor link 406 as described above regarding the retractor link 280 (FIG. 20) is movable between a non-deformed condition and a deformed condition. In the non-deformed condition, the proximal portion 406*b* of the retractor link 406 bends outwardly from the longitudinal axis defined by the distal portion 406*a* of the retractor link 406 and outwardly of the knife slot 52 (FIG. 4) of the cartridge body 50. When the actuation sled assembly 400 is advanced through the knife slot 52 of the cartridge body 50, the proximal portion 406*b* of the retractor link 406 engages an inner wall of the cartridge body 50 defining the knife slot 52 and is moved to the deformed condition in which the distal and proximal portions 406*a* and 406*b* of the retractor link 406 are longitudinally aligned.

The drive assembly 500 (FIG. 26) is like the drive assemblies 98 (FIG. 13) and 298 (FIG. 22) and includes a working member 502 and a flexible drive beam 504 (FIG. 27). The distal portion of the flexible drive beam 504 defines a recess or opening 506 (FIG. 27) that receives the bend 434 in the proximal portion 406*b* of the retractor link 406 when the retractor link 406 is deformed. The working member 502 of the drive assembly 500 defines a distally facing pocket 510 (FIG. 27) that receives the upper portion of the body portion 422 and knife 426 of the knife bar 404 (FIG. 26) when the working member 502 is moved into engagement with the knife bar 404.

The actuation sled assembly 400 and the drive assembly 500 function in the same manner as the actuation sled assembly 266 and the drive assembly 298 described above except that the actuation sled 402 is only in abutting relation to the knife bar 404 and does not return to the retracted position with the knife bar 404 as the knife bar 404 is moved from the advanced position to the retracted position with the drive assembly 500. More specifically, when the drive assembly 500 moves from the drive assembly clamped position towards the drive assembly advanced position to move the actuation sled assembly 400 from the sled retracted position towards the sled advanced position, the retractor link 406 moves into the knife slot 52 (FIG. 4) and is deformed from the undeformed condition to the deformed condition. When this occurs, the bend 434 of the retractor link 406 is received in the opening 506 of the drive assembly 500 to couple the drive assembly 500 with the knife bar 404. As the drive assembly 500 moves towards the advanced position in the direction of arrow "H" in FIG. 26, the working member 502 of the drive assembly 500 engages the actuation sled 402 to move the actuation sled 402 from the sled retracted position to the sled advanced position to eject staples 60 (FIG. 4) from the staple cartridge 42. It is noted that when the working member 502 of the drive assembly 500 is engaged with the knife bar 404, the knife 426 of the knife bar 404 is received within the pocket 510 defined in the working end 502 of the drive assembly 500. In addition, when the knife bar 404 is engaged with the actuation sled 402, the base portion 424 of the knife bar 404 is received in the cutout 420 defined by the actuation sled 402. When the base portion 424 (FIG. 24) of the knife bar 404 is received in the cutout 420 (FIG. 25) of the actuation sled 402, the base portion 424 is supported on the flat surface 416*a* of the member 416 such that the rib 414 of the actuation sled 402 is received within the channel 428 defined in the base portion 424 of the knife bar 404.

FIG. 27 illustrates the distal portion of the tool assembly 16 (FIG. 1) as the drive assembly 500 is moved in the direction of arrow "I" from the advanced position back towards the retracted position. As the drive assembly 500 is retracted, the knife bar 404 which is coupled to the drive assembly 500 by the retractor link 406 also moves towards the retracted position. However, the actuation sled 402 which is only in abutting relation to the knife bar 404 disengages from the knife bar 404 and remains in the distal portion of the staple cartridge 42. (FIG. 27).

Figure 28:
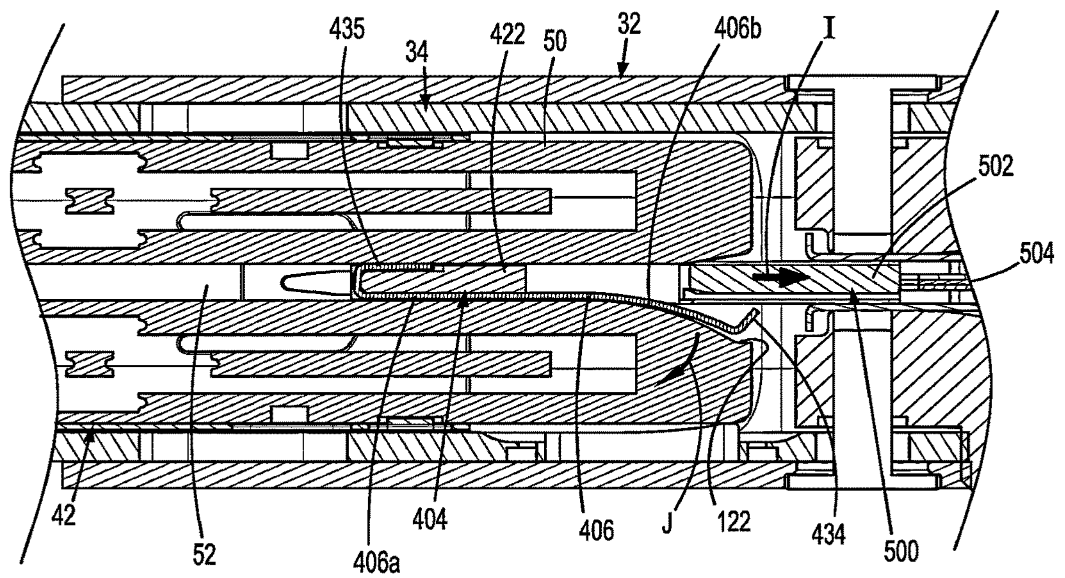
FIG. 28 is a cross-sectional view taken through the proximal portion of the tool assembly with the stapling device in the clamped and fired position and the drive assembly in the retracted position with the knife bar uncoupled from the drive assembly.

FIG. 28 illustrates the proximal portion of the tool assembly 16 as the drive assembly 500 approaches the retracted position. When the drive assembly 500 nears the retracted position, the proximal portion 406*b* of the retractor link 406 becomes aligned with the pocket 122 in the cartridge body 50 of the staple cartridge 42 and returns to the non-deformed condition in the direction of arrow "J" to disengage the knife bar 404 from the drive assembly 500. When this occurs, the drive assembly 500 continues to move to the retracted position independently of the knife bar 404. Disengaging the knife bar 404 from the drive assembly 500 allows for removal and replacement of the staple cartridge 42 to facilitate reuse of the stapling device 10 (FIG. 1).

Persons skilled in the art will understand that the devices and methods specifically described herein and illustrated in the accompanying drawings are non-limiting exemplary aspects of the disclosure. It is envisioned that the elements and features illustrated or described in connection with one exemplary embodiment may be combined with the elements and features of another without departing from the scope of the disclosure. As well, one skilled in the art will appreciate further features and advantages of the disclosure based on the above-described aspects of the disclosure. Accordingly, the disclosure is not to be limited by what has been particularly shown and described, except as indicated by the appended claims.

What is claimed is:

1. An actuation sled assembly for a surgical device, comprising:

an actuation sled comprising a central portion and one or more wedge members;

a knife bar coupled to the actuation sled; and a retractor link having a proximal portion and a distal portion, with the distal portion secured to the knife bar and extending longitudinally;

wherein the retractor link defines:

a non-deformed condition in which the proximal portion bends away from the distal portion and the knife bar, and a deformed condition in which the proximal portion is longitudinally aligned with the distal portion, with the retractor link biased toward the non-deformed condition, and wherein the distal portion of the retractor link is secured to the knife bar in both the non-deformed condition and in the deformed condition.

2. The actuation sled assembly of claim 1, wherein the knife bar comprises a longitudinally extending recess, with the distal portion of the retractor link secured within the longitudinally extending recess.

3. The actuation sled assembly of claim 1, wherein the proximal portion of the retractor link comprises an engaging member configured to engage a drive assembly of the surgical device, the engaging member comprising one of a 90-degree bend or a rounded protrusion.

4. The actuation sled assembly of claim 3, wherein the engaging member is disposed on a side of the retractor link facing the knife bar.

5. The actuation sled assembly of claim 3, wherein the engaging member of the retractor link is configured to engage the drive assembly when moving to the deformed condition.

6. The actuation sled assembly of claim 5, wherein the engaging member of the retractor link is configured to disengage from the drive assembly when moving to the non-deformed condition.

7. The actuation sled assembly of claim 6, wherein the central portion of the actuation sled comprises a cutout for slidable insertion of the knife bar.

8. The actuation sled assembly of claim 1, wherein the knife bar comprises:
a body secured to the actuation sled; and
a knife carried by the body and having a distally facing cutting edge.

9. The actuation sled assembly of claim 1, wherein the proximal portion of the retractor link extends proximally beyond the actuation sled.

10. A staple cartridge for a surgical device, comprising:
a cartridge body defining a knife slot;
a plurality of staples carried by the cartridge body; and
an actuation sled assembly disposed within the cartridge body and comprising:
an actuation sled comprising a central portion and one or more wedge members;
a knife bar coupled to the actuation sled and movable through the knife slot; and
a retractor link having a proximal portion and a distal portion, with the distal portion secured to the knife bar and extending longitudinally;
wherein the retractor link defines:
a non-deformed condition in which the proximal portion bends away from the distal portion and the knife bar, and
a deformed condition in which the proximal portion is longitudinally aligned with the distal portion, with the retractor link biased toward the non-deformed condition, and
wherein the distal portion of the retractor link is secured to the knife bar in both the non-deformed condition and in the deformed condition.

11. The staple cartridge of claim 10, wherein the cartridge body further comprises a curved inner wall defining a pocket, and wherein the retractor link is configured to extend into the pocket when in the non-deformed condition.

12. The staple cartridge of claim 11, wherein the retractor link is configured to disengage the knife bar from a drive assembly of the surgical device when moving to the non-deformed condition and into the pocket.

13. The staple cartridge of claim 12, wherein the retractor link is configured to engage the knife bar with the drive assembly of the surgical device when moving to the deformed condition and out of the pocket.

14. The staple cartridge of claim 10, wherein the proximal portion of the retractor link extends proximally beyond the actuation sled.

15. A surgical stapling device, comprising:
a tool assembly, comprising:
an anvil;
a staple cartridge having a cartridge body defining a knife slot, a plurality of staples carried by the cartridge body, and an actuation sled assembly disposed within the cartridge body, the actuation sled assembly comprising:
an actuation sled comprising a central portion and one or more wedge members;
a knife bar coupled to the actuation sled and movable through the knife slot; and
a retractor link having a proximal portion and a distal portion, with the distal portion secured to the knife bar and extending longitudinally, wherein the retractor link defines a non-deformed condition in which the proximal portion bends away from the distal portion and the knife bar, and a deformed condition in which the proximal portion is longitudinally aligned with the distal portion, with the retractor link biased toward the non-deformed condition; and
a drive assembly selectively coupled with the knife bar and movable between a retracted position and an advanced position to eject the plurality of staples;
wherein the retractor link is configured to disengage the knife bar from the drive assembly when in the non-deformed condition, and
wherein the distal portion of the retractor link is secured to the knife bar in both the non-deformed condition and in the deformed condition.

16. The surgical stapling device of claim 15, wherein the knife bar comprises a longitudinally extending recess, with the distal portion of the retractor link secured within the longitudinally extending recess.

17. The surgical stapling device of claim 15, wherein the proximal portion of the retractor link comprises an engaging member configured to selectively engage the drive assembly, the engaging member comprising one of a 90-degree bend or a rounded protrusion.

18. The surgical stapling device of claim 15, wherein the cartridge body further comprises a curved inner wall defining a pocket, and wherein the retractor link is configured to extend into the pocket when in the non-deformed condition.

19. The surgical stapling device of claim 18, wherein the retractor link is configured to move into the pocket to the non-deformed condition, disengaging the knife bar from the drive assembly, when the drive assembly moves to the retracted position.

20. The surgical stapling device of claim 19, wherein the retractor link is configured to move out of the pocket to the deformed condition, engaging the knife bar with the drive assembly, when the drive assembly moves to the advanced position.

* * * * *